US012767971B2

(12) United States Patent
Houston et al.

(10) Patent No.: US 12,767,971 B2
(45) **Date of Patent: *Oct. 20, 2026**

(54) METHOD TO PRODUCE RETINYL ACETATE

(71) Applicant: DSM IP ASSETS B.V., Heerlen (NL)

(72) Inventors: Peter Louis Houston, Kaiseraugst (CH); Valmik Kanubhai Vyas, Kaiseraugst (CH); Anna Symbor-Nagrabska, Kaiseraugst (CH); Reed Chadbourne Doten, Kaiseraugst (CH); Christopher Mark Farrell, Kaiseraugst (CH); Ethan Lam, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 310 days.

This patent is subject to a terminal disclaimer.

(21) Appl. No.: 18/292,227

(22) PCT Filed: Jul. 27, 2021

(86) PCT No.: PCT/EP2021/070909

§ 371 (c)(1),
(2) Date: Jan. 25, 2024

(87) PCT Pub. No.: WO2023/006179

PCT Pub. Date: Feb. 2, 2023

(65) Prior Publication Data

US 2024/0279706 A1 Aug. 22, 2024

(51) Int. Cl.
*C12P 23/00* (2006.01)
*C12N 1/16* (2026.01)
*C12N 9/10* (2006.01)

(52) U.S. Cl.
CPC ................ *C12P 23/00* (2013.01); *C12N 1/16* (2013.01); *C12N 9/1029* (2013.01)

(58) Field of Classification Search
None
See application file for complete search history.

(56) References Cited

U.S. PATENT DOCUMENTS 11,578,344 B2 * 2/2023 Balch ............... C12Y 203/0102

FOREIGN PATENT DOCUMENTS

| | | | |
|---|---|---|---|
| WO | 2006102342 | A2 | 9/2006 |
| WO | 2011153378 | A1 | 12/2011 |
| WO | 2013022989 | A2 | 2/2013 |
| WO | 2013110673 | A1 | 8/2013 |
| WO | 2014096992 | A1 | 6/2014 |
| WO | 2014122227 | A2 | 8/2014 |
| WO | 2015007748 | A1 | 1/2015 |
| WO | 2016172282 | A1 | 10/2016 |
| WO | 2019058001 | A1 | 3/2019 |
| WO | 2020141168 | A1 | 7/2020 |

OTHER PUBLICATIONS

Il'chenko, AP; et al; "Ethanol Metabolism in the Yeasts *Yarrowia* and *Torulopsis*: A Review" Applied Biochemistry and Microbiology, 41, 426-432, 2005 (Year: 2005).*
Ausubel et al., "Current Protocols in Molecular Biology", Online: https://currentprotocols.onlinelibrary.wiley.com/journal/19343647, 1998, 5 pages.
Balch et al., "Lachancea mirantina acetyl transferase 1 (LrnATF1), SEQ:13.", 2019, 1 page.
Dujon et al., "Genome evolution in yeasts", Nature, vol. 430, Jul. 2004, 10 pages.
Finogenova et al., "Organic Acid Production by the Yeast *Yarrowia lipolytica*: A Review of Prospects", Applied Biochemistry and Microbiology, vol. 41, No. 5, 2005, pp. 418-425.
Goncalves et al., "Yarrowia lipolytica and Its Multiple Applications in the Biotechnological Industry", Hindawi Publishing Corporation, The Scientific World Journal, vol. 2014, Art. 476207, Published Mar. 13, 2014, 15 pages.
Houston et al., "Lachancea mirantina ATF1 protein, SEQ ID 1.", 2020, 1 page.
Needleman et al., "A General Method Applicable to the Search for Similarities in the Amino Acid Sequence of Two Proteins", Department of Biochemistry, Northwestern University, and Nuclear Medicine Service, V. A. Research Hospital Chicago, 11 pages.
Rice et al., "EMBOSS: The European Molecular Biology Open Software Suite", TIG, vol. 16, No. 6, Jun. 2000, 2 pages.
Sambrook et al., "Molecular Cloning", A Laboratory Manual, Second Edition, 1989, 30 pages.
ScanProsite User Manuel, Online: file:///O:/_New%20Apps%20PTO%20Efilings/_DSM/4662/4662-4662/REFS/Prosite.html, 27 pages, Retrieved Jan. 17, 2024.
International Search Report for PCT/EP2021/070909 mailed Nov. 24, 2021, 4 pages.
Written Opinion of the ISA for PCT/EP2021/070909 mailed Nov. 24, 2021, 5 pages.

* cited by examiner

*Primary Examiner* — David W Berke-Schlessel
(74) *Attorney, Agent, or Firm* — Nixon & Vanderhye, PC

(57) ABSTRACT

The present invention is related to a novel process for production of retinyl acetate in a host cell, particularly oleaginous yeast such as e.g. *Yarrowia*, wherein the product purity could be increased with reduction of unwanted side-products. Particularly, the novel process comprises fermentation in the presence of ethanol, such as e.g. in a fed-batch fermentation process. Such process is especially useful in a biotechnological process for production of vitamin A.

13 Claims, No Drawings

Specification includes a Sequence Listing.

SEQUENCE LISTING

```
<160> NUMBER OF SEQ ID NOS: 18

<210> SEQ ID NO 1
<211> LENGTH: 334
<212> TYPE: PRT
<213> ORGANISM: Yarrowia lipolytica

<400> SEQUENCE: 1

Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
            20                  25                  30

Arg Val Tyr Thr Ser Thr Glu Thr Ser His Ile Asp Gln Glu Ser Tyr
        35                  40                  45

Asn Phe Phe Glu Lys Tyr Ala Arg Leu Ala Asn Ile Gly Tyr Cys Val
    50                  55                  60

Gly Pro Gly Thr Lys Ile Phe Lys Pro Phe Asn Cys Gly Leu Gln Cys
```

```
65                  70                  75                  80

Ala His Phe Pro Asn Val Glu Leu Ile Glu Glu Phe His Asp Pro Arg
                85                  90                  95

Leu Ile Phe Asp Val Ser Gly Tyr Leu Ala Val Asp His Ala Ser Lys
            100                 105                 110

Gln Ile Tyr Leu Val Ile Arg Gly Thr His Ser Leu Glu Asp Val Ile
        115                 120                 125

Thr Asp Ile Arg Ile Met Gln Ala Pro Leu Thr Asn Phe Asp Leu Ala
    130                 135                 140

Ala Asn Ile Ser Ser Thr Ala Thr Cys Asp Asp Cys Leu Val His Asn
145                 150                 155                 160

Gly Phe Ile Gln Ser Tyr Asn Asn Thr Tyr Asn Gln Ile Gly Pro Lys
                165                 170                 175

Leu Asp Ser Val Ile Glu Gln Tyr Pro Asp Tyr Gln Ile Ala Val Thr
            180                 185                 190

Gly His Ser Leu Gly Gly Ala Ala Ala Leu Leu Phe Gly Ile Asn Leu
        195                 200                 205

Lys Val Asn Gly His Asp Pro Leu Val Val Thr Leu Gly Gln Pro Ile
    210                 215                 220

Val Gly Asn Ala Gly Phe Ala Asn Trp Val Asp Lys Leu Phe Phe Gly
225                 230                 235                 240

Gln Glu Asn Pro Asp Val Ser Lys Val Ser Lys Asp Arg Lys Leu Tyr
                245                 250                 255

Arg Ile Thr His Arg Gly Asp Ile Val Pro Gln Val Pro Phe Trp Asp
            260                 265                 270

Gly Tyr Gln His Cys Ser Gly Glu Val Phe Ile Asp Trp Pro Leu Ile
        275                 280                 285

His Pro Pro Leu Ser Asn Val Val Met Cys Gln Gly Gln Ser Asn Lys
    290                 295                 300

Gln Cys Ser Ala Gly Asn Thr Leu Leu Gln Gln Val Asn Val Ile Gly
305                 310                 315                 320

Asn His Leu Gln Tyr Phe Val Thr Glu Gly Val Cys Gly Ile
                325                 330


<210> SEQ ID NO 2
<211> LENGTH: 1005
<212> TYPE: DNA
<213> ORGANISM: Yarrowia lipolytica

<400> SEQUENCE: 2

atgaagcttt ccaccatcct cttcacagcc tgcgctaccc tggctgccgc cctcccttcc     60

cccatcactc cttctgaggc cgcagttctc cagaagcgag tgtacacctc taccgagacc    120

tctcacattg accaggagtc ctacaacttc tttgagaagt acgcccgact cgcaaacatt    180

ggatattgtg ttggtcccgg cactaagatc ttcaagccct tcaactgtgg cctgcaatgt    240

gcccacttcc ccaacgttga gctcatcgag gagttccacg acccccgtct catctttgat    300

gtttctggtt acctcgctgt tgatcatgcc tccaagcaga tctaccttgt tattcgagga    360

acccactctc tggaggacgt cataaccgac atccgaatca tgcaggctcc tctgacgaac    420

tttgatcttg ctgctaacat ctcttctact gctacttgtg atgactgtct tgtccacaat    480

ggcttcatcc agtcctacaa caacacctac aatcagatcg gccccaagct cgactctgtg    540

attgagcagt atcccgacta ccagattgct gtcaccggtc actctctcgg aggagctgca    600

gcccttctgt tcggaatcaa cctcaaggtt aacggccacg atcccctcgt tgttactctt    660
```

```
ggtcagccca ttgtcggtaa cgctggcttt gctaactggg tcgataaact cttctttggc    720

caggagaacc ccgatgtctc caaggtgtcc aaagaccgaa agctctaccg aatcacccac    780

cgaggagata tcgtccctca agtgcccttc tgggacggtt accagcactg ctctggtgag    840

gtctttattg actggcccct gatccaccct cctctctcca acgttgtcat gtgccagggc    900

cagagcaata aacagtgctc tgccggtaac actctgctcc agcaggtcaa tgtgattgga    960

aaccatctgc agtacttcgt caccgagggt gtctgtggta tctaa                   1005


<210> SEQ ID NO 3
<211> LENGTH: 498
<212> TYPE: PRT
<213> ORGANISM: Yarrowia lipolytica

<400> SEQUENCE: 3

Met Pro Leu Glu Leu Pro Ser Leu Asn Ala Ser Ile Val Gly Asn Thr
1               5                   10                  15

Val Gln Asn Gly Ala Val Glu Gln Phe Leu Asn Ile Arg Tyr Ala Asp
            20                  25                  30

Ile Pro Gly Lys Phe Glu Lys Pro Val Leu Lys Asn Asp Trp Asn Gly
        35                  40                  45

Ala Glu Ile Asp Ala Thr Lys Val Gly Pro Val Cys Pro Gln Pro Arg
    50                  55                  60

Thr Pro Phe Asn Phe Phe Ser Val Pro Asp Asp Leu Trp Glu Lys Val
65                  70                  75                  80

Asn Val Asp Thr Tyr Gln Asp Gly Leu Leu Cys Asp Asn Leu Ile Val
                85                  90                  95

Thr Arg Pro Lys Gly Val Ser Ala Asn Ala Arg Leu Pro Thr Val Val
            100                 105                 110

Trp Ile His Gly Gly Ser Asn Ile Glu Gly Ser Ile Tyr Asn Leu Ile
        115                 120                 125

Tyr Glu Pro Gln Phe Leu Val Ala Glu Ser Val Arg Val Gly Lys Pro
    130                 135                 140

Ile Val His Val Cys Ile Glu Tyr Arg Leu Gly Leu Ala Gly Phe Leu
145                 150                 155                 160

Thr Lys Asn Gly Lys Gly Asn Trp Gly Thr Trp Asp Gln Tyr Thr Gly
                165                 170                 175

Cys Gln Trp Val Asn Arg His Ile Gln Asp Phe Gly Gly Asp Pro Leu
            180                 185                 190

Asn Val Thr Leu Thr Gly Glu Ser Ala Gly Ser Val Ala Val His Asn
        195                 200                 205

Met Leu Ile Lys Asp Ser Met Asn Gly Arg Lys Leu Phe Arg Asn Ala
    210                 215                 220

Val Met Met Ser Gly Thr Leu Glu Thr Ile Thr Pro Gln Pro Pro Lys
225                 230                 235                 240

Trp His Ala Arg Leu Glu Glu Lys Val Ala Lys Val Thr Gly Lys Glu
                245                 250                 255

Val Ala Asp Leu Ala Ser Leu Ser Asp Lys Glu Leu Leu Asp Ala Gln
            260                 265                 270

Ile Lys Leu Asn Val Ala Val Cys Met Thr Cys Asp Asp Gly Asp Phe
        275                 280                 285

Phe Glu Pro Gly Trp Lys Gln His Leu Thr Pro Asp Trp Leu Asp Lys
    290                 295                 300

Leu Ile Ile Ser Asp Cys Lys Asp Glu Gly Met Leu Tyr Phe Leu Pro
```

-continued

```
305                 310                 315                 320

Val Asn Ala Gln Asp Asp Glu Glu Leu Leu Ala Lys Val Ala Lys Ser
                325                 330                 335

Pro Val Gly Lys Glu Ile Ser Glu Leu Tyr Gly Ile Lys Glu Gly Gly
            340                 345                 350

Asp Ile Lys Ser Ala Cys Leu Asp Leu Lys Thr Asp Ala Thr Phe Asn
        355                 360                 365

Tyr Phe Asn His Leu Leu Phe Lys Lys Met Glu Glu Ala Arg Asn Asn
    370                 375                 380

Gly Ser Thr Ser Arg Val Tyr Arg Leu Ala Val Asp Glu Pro Asn Pro
385                 390                 395                 400

His Asn Pro Asp Gln Arg Ala His His Ala Val Asp Val Leu Tyr Met
                405                 410                 415

Phe Asn Ser Thr Lys Phe Asn Glu His Gly Asp Lys Leu Ser Arg Leu
            420                 425                 430

Phe Gln Ser His Phe Leu Arg Leu Ala Tyr Gly Leu Glu Pro Trp Asp
        435                 440                 445

His Arg Asn Phe Gly Val Tyr Arg Asn Gly Gly Tyr Gln Gln Leu Pro
    450                 455                 460

Leu Ser Glu Leu Asn Lys Val Arg Pro Val Glu Arg Tyr Glu Ala Leu
465                 470                 475                 480

Ser Lys Met Asp Phe Gly Gln Val Gly Arg Leu Ser Asn Ala Leu Ser
                485                 490                 495

Arg Leu


<210> SEQ ID NO 4
<211> LENGTH: 1497
<212> TYPE: DNA
<213> ORGANISM: Yarrowia lipolytica

<400> SEQUENCE: 4

atgcctctcg aactcccctc gctcaacgcc tcgattgtcg gcaacaccgt tcagaacggc      60

gctgttgagc agtttctcaa catccgatac gccgacattc ctggcaagtt tgagaagccc     120

gtgctcaaga acgattggaa cggcgcggag atcgacgcca ccaaggtcgg tcccgtgtgc     180

ccccaacccc gcaccccatt caacttcttc tccgtgccag acgacctctg ggagaaagtc     240

aatgtggaca cgtaccagga cggtctgctg tgcgacaacc tgattgtgac gcgaccgaag     300

ggcgtgtctg ccaacgcccg gctgcccact gttgtgtgga tccacggcgg ctccaatatt     360

gagggcagta tctacaacct catctatgag ccccagttcc tggtggcaga gtcggtgcga     420

gtaggcaagc cgattgtgca cgtgtgtatc gagtaccgac tgggtctcgc gggcttcctc     480

accaagaacg gcaagggcaa ctggggcacg tgggatcagt acacgggctg ccagtgggtc     540

aaccgccaca ttcaggactt tggaggcgat cctttgaacg tgacattgac cggtgagtct     600

gccggctctg tagcagtcca taacatgctc atcaaggact ccatgaacgg ccgaaagttg     660

ttccgaaatg ccgtcatgat gagtggcact ctcgagacca tcactcctca gcctcccaag     720

tggcatgctc gtttggagga gaaggtggcc aaggtcactg gcaaggaagt ggccgacctt     780

gcttctctgt ccgataagga gctgctcgac gcccagatca agctcaatgt ggctgtgtgc     840

atgacttgcg acgacggcga ctttttcgag cccggatgga agcagcatct gactcctgac     900

tggctcgaca agctcatcat ctccgattgc aaggacgagg gcatgctgta tttcctgcca     960

gtcaacgcgc aggacgacga ggagctgttg gcaaaggtgg ccaagtcgcc cgtgggtaag    1020
```

gagatttccg agctttacgg catcaaggag ggtggcgata tcaagtctgc gtgtctcgat 1080
ctcaagactg acgccacctt caattacttt aaccatctgc tgttcaagaa gatggaggag 1140
gcccgaaaca acggctccac ttctcgagtt taccgtctgg ccgtcgatga gcccaacccc 1200
cacaaccccg accagcgggc ccaccacgcc gtcgacgtgc tgtacatgtt caactcgacc 1260
aagttcaacg agcacggcga caagctgtct cggctgttcc agagccactt tttgcggctg 1320
gcgtatggcc tggagccctg ggaccatcga aactttggag tgtacagaaa cggcggctac 1380
cagcagctgc cgctgagtga gttgaacaag gtccgacccg tcgagcggta cgaggcgctg 1440
tccaagatgg actttggcca ggttgggcgt ttgtccaatg cgctttcgcg cctatga 1497

<210> SEQ ID NO 5
<211> LENGTH: 406
<212> TYPE: PRT
<213> ORGANISM: Yarrowia lipolytica

<400> SEQUENCE: 5

Met Ala Gly Phe Asn Phe Thr Phe Gly Gln Val Ile Ser Tyr Leu Ala
1 5 10 15

Ser Met Leu Tyr Gly Gln Val Asp Ala Thr Ser Ser Ser Thr Arg Ile
20 25 30

Gln Ala Thr Gln Asp Leu Tyr Asp Phe Thr Ala Lys Phe Ser Arg Leu
35 40 45

Ser Asn Ile Ala Tyr Cys Ile Asn Ala Pro Phe Thr Pro Leu Arg Thr
50 55 60

Asp Phe Thr Cys Gly Glu Ser Cys Arg Tyr Phe Pro Asp Leu Gln Leu
65 70 75 80

Asp Ser Val Phe Gly Gly Asn Phe Ser Ser Ala Ser Thr Thr Gly Tyr
85 90 95

Ile Ala Tyr Asp His Lys Lys Lys Glu Lys Tyr Ile Val Phe Arg Gly
100 105 110

Thr Phe Ser Ile Pro Asp Ile Ile Thr Asp Ile Gln Phe Gln Thr Ala
115 120 125

Pro Trp Leu Thr Ser Leu Pro Thr His Leu Ile Pro Thr Lys Glu Asp
130 135 140

Phe Glu His Lys Gln Ala Ile Leu Lys His Tyr Ala Ala Glu Asn Lys
145 150 155 160

Gly Leu Ser Asn Leu Glu Glu Arg Gln Asp Val Val His Glu Asp Pro
165 170 175

Ser Leu Val Pro Lys Lys Met Asp Lys Cys Glu Asn Cys Gln Ile His
180 185 190

Asp Gly Phe Ala Lys Gly Phe Asn Glu Thr Ile Glu His Ala Gly Pro
195 200 205

Gln Ile Glu Lys Phe Leu Gly Asn Asn Thr Asp Tyr Lys Met Phe Val
210 215 220

Val Gly His Ser Leu Gly Ala Ala Gln Ala Gln Leu Phe Ala Thr Gln
225 230 235 240

Phe Lys Leu Leu Gly Phe Asp Pro Tyr Met Ile Asn Phe Gly Gln Pro
245 250 255

Arg Leu Gly Asn Pro Glu Phe Ala Ala Tyr Ile Asn Gln Leu Trp Phe
260 265 270

Asn Asp Thr Gly Leu Val Val Asn Asp Ala Arg Arg Phe Tyr Arg Val
275 280 285

Thr His Trp Asn Asp Ile Val Val Gly Val Pro Asp Trp Leu Asn Tyr

-continued 290 295 300

Thr His Ser Ile Gly Glu Val Phe Ile Asp Glu Glu Ser Val Tyr Pro
305 310 315 320

Lys Leu Asp Lys Val Val Val Cys Glu Gly Gly Glu Asn Pro Leu Cys
325 330 335

His Arg Gly Thr Phe Asn Leu Trp Ser Arg Ile Asn Phe Leu Gln Asn
340 345 350

His Leu Ala Tyr Ile Phe Tyr Ile Gly Leu Cys Ala Phe Asn Ile Gly
355 360 365

Arg Arg Asp Val Leu Asn Met Pro Gln Tyr Gln Gly Asn Phe Ser Tyr
370 375 380

Gln His Asn Ile Asp Pro Asn Tyr Asn Tyr Asp Thr Lys Val Pro Thr
385 390 395 400

Arg Ile Ser Lys Ser Asn
405

<210> SEQ ID NO 6
<211> LENGTH: 1221
<212> TYPE: DNA
<213> ORGANISM: Yarrowia lipolytica

<400> SEQUENCE: 6
atggcagggt tcaacttcac tttcgggcag gtgatttcgt acctggcttc catgctctat 60
ggacaggtgg atgccacttc atcctccact cgaatccagg ccacccagga tctgtacgac 120
ttcacagcca agttttcgcg actctcaaac atcgcgtact gcatcaatgc cccccttcacg 180 cctctcagaa cggacttcac ctgcggagaa agctgtcggt acttccccga cctccagctg 240
gactcagtgt ttggtggtaa cttctcctca gcctccacta ccggctacat tgcatacgac 300
cacaagaaga aggaaaagta cattgtgttt cgaggaactt tcagtatccc tgatatcatc 360
acagacattc aatttcagac tgccccttgg ttgacctctc tgcccacgca tctgatccct 420
accaaggagg actttgaaca caagcaggcc atcctgaagc actacgctgc cgaaaacaag 480
ggtctcagca acctggaaga gcgacaggat gttgtgcatg aagaccctag cctggttccc 540
aagaaaatgg acaagtgcga gaactgccag atccatgacg gattcgccaa gggcttcaac 600
gagactatcg agcatgccgg accccagatt gaaaagttcc tgggcaataa caccgactac 660
aagatgtttg ttgttggcca ctctctagga gctgctcagg cccagctgtt tgctacacag 720
ttcaaactgc tgggatttga cccttacatg atcaactttg gacagcctcg acttggaaac 780
cctgagttcg ccgcctacat caaccagctg tggttcaacg atactggtct ggttgtcaat 840
gatgcccgac gattctaccg agtgactcac tggaacgata tcgtcgtggg agtgcccgac 900
tggctcaatt acacccactc tatcggagag gtgttcatag acgaggagag cgtttacccc 960
aagctggaca aggtggtggt gtgcgaggga ggagagaacc ccctgtgcca ccgaggaact 1020
ttcaacctgt ggtcacgaat caacttcctg cagaaccatt tggcttatat cttctacatt 1080
ggtctgtgtg ctttcaacat tggccgaaga gacgtgctca acatgccaca ataccagggc 1140
aacttctcgt accagcacaa catcgacccc aactacaatt acgataccaa ggttcccacc 1200
cggatcagta aatcaaacta a 1221

<210> SEQ ID NO 7
<211> LENGTH: 371
<212> TYPE: PRT
<213> ORGANISM: Yarrowia lipolytica

<400> SEQUENCE: 7

Met Val Ser Leu Ser Ala Arg Ile Lys Asp Phe Phe Ser Val Leu Leu
1 5 10 15

Leu Gly Ala Ala Thr Ile Thr Pro Ser Thr Gln Thr Ala Gly Val Ser
20 25 30

Gln Gly Phe Tyr Asp Phe Ala Arg Asp Phe Ala His Leu Ser Asn Ile
35 40 45

Ala Tyr Cys Val Asn Ala Pro Ile Thr Pro Leu Asn Pro Asp Phe Thr
50 55 60

Cys Gly Asn Ser Cys Lys His Phe Pro Glu Ile Glu Leu Val Lys Thr
65 70 75 80

Phe Gly Gly Asn Phe Phe Lys Thr Ser Ile Thr Gly Tyr Leu Ala Val
85 90 95

Asp His Val Lys Lys Glu Lys Tyr Val Val Phe Arg Gly Thr Phe Ser
100 105 110

Leu Ala Asp Ala Ile Thr Asp Met Gln Phe Gln Leu Ser Pro Phe Leu
115 120 125

Val Asp Val Pro Ala Leu Asn Thr Phe Ser Ala Asn Asp Thr Thr Ala
130 135 140

Glu Ala Gln Thr His Cys Glu Gly Cys Lys Ile His Asp Gly Phe Ser
145 150 155 160

Lys Ala Phe Thr Glu Thr Trp Gly Asn Ile Gly Glu Asp Leu Gln Lys
165 170 175

His Leu Asp Ala Asn Pro Asp Tyr Gln Leu Tyr Val Thr Gly His Ser
180 185 190

Leu Gly Ala Ala Met Ala Leu Leu Gly Ala Thr Ser Ile Lys Leu Lys
195 200 205

Gly Tyr Asp Pro Ile Leu Ile Asn Tyr Gly Gln Pro Arg Val Gly Asn
210 215 220

Lys Pro Phe Ala Glu Phe Ile Asn Lys Leu Trp Phe Gly Glu Gly Asn
225 230 235 240

Gly Leu Glu Ile Thr Pro Glu Arg Lys Leu Tyr Arg Met Thr His Trp
245 250 255

Asn Asp Ile Phe Val Gly Leu Pro Asn Trp Glu Gly Tyr Thr His Ser
260 265 270

Asn Gly Glu Val Tyr Ile Asn Asn Arg Phe Ile Asn Pro Pro Leu Lys
275 280 285

Asp Val Ile Ser Cys Ala Gly Gly Glu Asn Ser Lys Cys Tyr Arg Ser
290 295 300

Ser Phe Ser Leu Leu Ser Gln Ile Asn Leu Leu Gln Asn His Leu Ala
305 310 315 320

Tyr Ile Asp Tyr Ile Gly Tyr Cys Ala Leu Asn Ile Gly Arg Arg Glu
325 330 335

Leu Ala Asp Gln Glu His Tyr Thr Gly Pro Tyr Tyr Tyr Gly His Arg
340 345 350

Ser Glu Glu Asp Phe Lys Lys Leu Gly Leu Glu Leu Ser Thr Pro Gln
355 360 365

Val Glu Asn
370

<210> SEQ ID NO 8
<211> LENGTH: 1116
<212> TYPE: DNA
<213> ORGANISM: Yarrowia lipolytica

<400> SEQUENCE: 8

```
atggtatccc tctctgctcg aatcaaagac tttttttcgg tcctcctcct cggagctgca      60
accatcactc cctccacaca gaccgcaggc gtgtctcaag ggttctatga ttttgctcgg     120
gactttgccc atctgtccaa cattgcctac tgtgtcaatg ctcccatcac tccactgaac     180
ccggacttca cctgtggcaa ctcgtgcaag cactttccgg aaattgagct tgtgaagaca     240
tttggaggca acttcttcaa gacctccatt acgggctacc tggctgtcga tcatgtcaag     300
aaggagaagt acgttgtctt ccgaggaacc ttttcgctgg cagacgcgat cacggacatg     360
cagttccagc tgtctccttt cctggtcgat gtgcctgccc tgaacacttt ctcagctaat     420
gacaccaccg cagaggccca gacgcactgt gagggctgca aaattcacga cggcttctcc     480
aaggccttta ccgagacctg ggtaacatt ggtgaggatc tgcagaaaca cctggacgct     540
aacccggact accagctgta cgtgactggc cattctctgg gagctgctat ggcccttctt     600
ggagctactt ccatcaagct caagggctac gatcccattc tcatcaacta cggacagccc     660
cgagtcggaa acaagccctt cgctgagttc attaacaagt tgtggtttgg agaaggcaac     720
ggtctggaaa tcacccccga gagaaagctg taccgaatga cccactggaa cgacatcttt     780
gttggcctgc ccaactggga gggatacacc cactctaacg gtgaagtata catcaacaac     840
cggttcatca accctcctct caaggatgtc atctcttgtg ctggaggcga aaactcgaag     900
tgctaccgat cctcgttcag cctgctgtcc cagatcaatc tgctccaaaa ccacctggct     960
tacattgatt acattggata ctgcgctctg aacattggtc gacgagagct tgccgatcag    1020
gaacattaca ctggtcctta ttactatggt catcgatctg aggaggactt taagaagttg    1080
ggcttggagc tatccacccc acaagttgag aactga                              1116
```

<210> SEQ ID NO 9
<211> LENGTH: 569
<212> TYPE: PRT
<213> ORGANISM: Yarrowia lipolytica

<400> SEQUENCE: 9

```
Met His Val Pro Val Leu Gly Arg Leu Glu Leu Ser His Trp Pro Met
1               5                   10                  15

Leu Phe Val Ser Leu Phe Leu Val Cys Leu Glu Phe Leu Val Ser Phe
            20                  25                  30

Ile Thr Ala Leu Leu Pro Asn Phe Phe Ile Glu Trp Cys His Asp Lys
        35                  40                  45

Val Glu Ile Leu Gln Val Tyr Phe Pro Ser Thr Gly Glu Val Ala Leu
    50                  55                  60

Arg Lys Ser Pro Glu Gln Leu Glu Thr Val Asn Ala Leu Leu Lys Ala
65                  70                  75                  80

Arg Asp Phe Val Glu Ile Cys Asp Phe His Gly Tyr Gln Ala Glu Glu
                85                  90                  95

His Val Val Gln Thr Lys Asp Gly Phe Leu Leu Gly Val His Arg Ile
            100                 105                 110

Leu Pro Lys Asn Pro Ala Ala Leu Leu Thr Asp Asp Pro Glu Val Leu
        115                 120                 125

Ser Thr Pro Ala Pro Pro Pro Ala Phe Leu Ala Gly Asn Leu Glu Val
    130                 135                 140

Tyr Ser Ser Pro Pro Lys Arg Gly Ser Lys Arg Ser Val Ser Ser Lys
145                 150                 155                 160
```

-continued

```
Leu Ile Thr Arg Pro Val Val Tyr Leu His His Gly Leu Leu Met Asn
                165                 170                 175

Ser Glu Val Trp Val Val Asn Thr Asp Ala Lys Lys Ser Ile Ala Phe
            180                 185                 190

Ala Leu Ala Asp Leu Gly Phe Asp Val Trp Leu Gly Asn Asn Arg Gly
        195                 200                 205

Asn Lys Tyr Ser Arg Lys His Met Lys Tyr Asn Pro Glu Ser Arg Glu
    210                 215                 220

Phe Trp Asp Phe Cys Leu Asp Asp Phe Ala Leu Phe Asp Ile Pro Asp
225                 230                 235                 240

Ser Ile Asp Tyr Ile Leu Ser Val Thr Lys Gln Lys Ser Leu Ser Tyr
                245                 250                 255

Ile Gly Phe Ser Gln Gly Ser Ala Gln Ala Phe Ala Ser Leu Ala Ile
            260                 265                 270

Arg Pro Pro Leu Asn Asp Lys Val Asn Leu Phe Ile Ala Val Ala Pro
        275                 280                 285

Ala Met Ser Pro Pro Gly Leu Arg Ser Lys Ile Val Asn Ser Leu Met
    290                 295                 300

Arg Ala Ser Pro Gln Leu Leu Phe Leu Cys Phe Gly Arg Arg Ala Ile
305                 310                 315                 320

Leu Ser Ser Ser Pro Phe Trp Glu Ser Val Leu Asp Ala Lys Leu Tyr
                325                 330                 335

Ala Arg Ile Ile Asp Ala Ala Cys Arg Met Leu Phe Asp Trp Tyr Gly
            340                 345                 350

Glu Asn Ile Thr Trp Pro Gln Lys Ile Ala Ala Tyr His His Leu Tyr
        355                 360                 365

Ser Tyr Thr Ser Val Lys Ser Val Val His Trp Phe Gln Ile Ile Arg
    370                 375                 380

Ala Ala Ser Phe His Met Phe Glu Asp Val Ile Asn Ser Pro Leu Asp
385                 390                 395                 400

Pro His Leu Cys Lys Tyr Ser Thr Val Thr Arg Tyr Pro Thr Glu Asn
                405                 410                 415

Ile Arg Thr Pro Ile Ala Leu Ile Tyr Gly Lys Thr Asp Ser Leu Val
            420                 425                 430

Asp Ile Asp Gln Met Leu Ser Thr Leu Pro Ser Ser Thr Ile Ala Phe
        435                 440                 445

Gly Val Pro Lys His Glu His Leu Asp Leu Leu Trp Gly Asp Glu Ala
    450                 455                 460

Asp Thr Leu Val Ile Pro Lys Ile Val Ala Leu Leu Asp Tyr Tyr Thr
465                 470                 475                 480

Pro Val Pro Arg Ser Asn Lys Ser Ser Ser Asp His Ile Ser Glu Arg
                485                 490                 495

Leu Phe Glu Pro Ala Asn Ser Lys Val Ser Gly Leu Gly Leu Ser Gln
            500                 505                 510

Asp Leu Lys Ser Pro Leu Ser Leu Lys Lys Arg Ser Leu Ser Asn Ser
        515                 520                 525

Ser Ser Ile Gln Asp Ser His Lys Val Gly Gly Asp Thr Asp Ser Val
    530                 535                 540

Leu Ser Leu Arg Asn Leu Thr Pro Lys Gly Tyr Ala Leu Gly Ser Ala
545                 550                 555                 560

Lys Pro Val Ser Gly Thr Leu Asn Pro
                565
```

<210> SEQ ID NO 10
<211> LENGTH: 1710
<212> TYPE: DNA
<213> ORGANISM: Yarrowia lipolytica

<400> SEQUENCE: 10

```
atgcacgtcc ccgttctagg acgtctcgag ctgtcacatt ggcccatgct gtttgtgtcg     60
ctcttcctcg tctgcctcga gtttctcgtg agcttcatca ccgctctgct ccccaacttc    120
ttcattgaat ggtgccacga caaggtcgag attctgcagg tctacttccc cagcaccggc    180
gaggttgctc tcagaaagtc tcccgagcag ctcgaaaccg tcaacgctct gctcaaggcc    240
cgagactttg ttgaaatctg cgatttccat ggctaccagg ccgaagaaca tgtggttcag    300
accaaggatg gatttctgct aggagtgcac cgaatcctgc ccaagaaccc tgctgctctg    360
ctcaccgacg accccgaagt cctcagcacc cccgcccctc ccccggcctt cctggctgga    420
aacctcgaag tctactcttc gccccccaaa agaggctcca agcgaagtgt gtcctccaaa    480
ctgatcaccc gacccgttgt ctaccttcac catggtctgc tgatgaactc ggaggtctgg    540
gttgtgaaca cggacgccaa aaagtcgatt gcttttgctc tggccgacct gggatttgac    600
gtctggctcg gaaacaacag aggcaacaag tactcgcgaa aacacatgaa atacaacccc    660
gagtcgcgcg agttctggga tttctgtctc gacgactttg cgctgtttga tatccccgat    720
tccattgact atattctgtc tgtgaccaaa cagaagtctc tgtcttacat tggattctcc    780
cagggttcag cccaggcatt tgcatctctg gctatccgac ctcctctcaa cgataaggtc    840
aacctattca ttgccgttgc ccccgccatg tctcctcctg gcctgagatc caagattgtc    900
aactccctca tgagagcttc tccacagctg ctgttcctct gctttggtcg aagagctatc    960
ttgtcatcct ctcccttctg ggagtcggtt ctggacgcaa aactgtatgc tcgaatcatc   1020
gatgctgcct gcagaatgct gtttgactgg tacggagaga acatcacctg gccccagaag   1080
attgcagcct accaccacct gtactcgtac acctctgtca agtccgtcgt gcattggttc   1140
cagatcatcc gagcagcctc cttccacatg tttgaggatg tcatcaactc tcccctggac   1200
cctcatctgt gcaagtactc cactgtcacc cgatacccca ccgagaacat tcggacaccc   1260
attgctctga tctacggcaa gaccgactcg ctggtggaca ttgaccagat gctgtctact   1320
ctaccctcat ccactattgc atttggagtc cccaaacatg agcatctcga tcttctgtgg   1380
ggagacgaag ccgacactct ggttatcccc aagattgtcg ctctgctcga ttattacaca   1440
cctgtgccca gaagtaacaa gagcagcagt gaccatatca gcgagcgtct atttgagcct   1500
gctaactcca aggtctcggg tctgggactc agccaggacc tcaagtcgcc attgtctttg   1560
aaaaagagat ctctctccaa ctcctcatcg atccaggact ctcataaggt cggaggagac   1620
acagactcgg ttctaagtct ccgaaacctc actcccaagg ggtacgctct tggaagtgcc   1680
aagccagtga gtggcactct caacccttga                                    1710
```

<210> SEQ ID NO 11
<211> LENGTH: 365
<212> TYPE: PRT
<213> ORGANISM: Yarrowia lipolytica

<400> SEQUENCE: 11

```
Met Leu Ser Leu Ile Ala Ile Phe Leu Leu Val Thr Thr Ala Leu Ala
1               5                   10                  15

Gln Thr Ala Asn Ile Thr Gln Ser Thr Tyr Asp Phe Val Leu Lys Tyr
            20                  25                  30
```

-continued

Gly Arg Leu Ser Asn Val Ala Tyr Cys Val Lys Ala Pro Gly Pro Tyr
35 40 45

Glu Leu Glu Thr Asp Phe Thr Cys Gly Arg Ser Cys Gly His Phe Pro
50 55 60

Asn Val Thr Leu Glu His Gln Phe Gly Gly Asp Phe Phe Ser Thr Ser
65 70 75 80

Ile Thr Gly Phe Leu Ala His Asp His Thr Lys Lys Glu Lys Tyr Ile
85 90 95

Val Phe Arg Gly Thr Phe Ser Leu Ala Asp Ala Ile Thr Asp Ala Leu
100 105 110

Phe Leu Gln Glu Pro Tyr Leu Ala Asp Leu Pro Pro Leu Asn Thr Thr
115 120 125

Asn Ile Asn Ser Thr Ser Asn Ser Ala Arg Val Asp Cys Pro Asp Cys
130 135 140

Glu Ile His Asp Gly Phe Gln Lys Ala Tyr Arg Glu Thr Met Val Asn
145 150 155 160

Met Gln Gly His Leu Val Ala Phe Leu Arg Asn Asn Thr Asp Tyr Lys
165 170 175

Leu Ile Val Thr Gly His Ser Leu Gly Ala Ala Thr Ala Leu Leu Met
180 185 190

Gly Ile Asn Leu Lys Asn Leu Gly Phe Asp Pro Met Val Ile Thr Phe
195 200 205

Gly Gln Pro Arg Val Gly Asn Lys Ala Phe Ala Asp Tyr Ala Asp Ser
210 215 220

Leu Phe Phe Lys Gln Gly Asp Asn Gly Leu Asn Ile Asn Pro Glu Arg
225 230 235 240

Arg Leu Tyr Arg Val Thr His Trp Asn Asp Ile Val Val Gly Val Pro
245 250 255

Phe Trp Ser Gly Tyr Thr His Thr Leu Gly Glu Val Tyr Ile Ser Tyr
260 265 270

Pro Asp Gly Val Asn Ala Pro Ile Glu Tyr Val Asn Ala Cys Ala Gly
275 280 285

Pro Asp Asn Asp Gln Cys His Tyr Gly Ser Phe Asp Leu Leu Ala Arg
290 295 300

Val Asn Ile Leu Lys Asn His Cys Ala Tyr Leu Asn Trp Ile Phe Tyr
305 310 315 320

Cys Ala Phe Asn Val Asp Lys Arg Gln Met Met Ile Asp Pro Pro Arg
325 330 335

Ile His Lys Arg Val Glu His Trp Ser Gly Lys Phe Ala Asp Val Glu
340 345 350

Phe Ser Glu Arg Met Ile Tyr Glu Ala Thr Tyr Pro Met
355 360 365

<210> SEQ ID NO 12
<211> LENGTH: 1243
<212> TYPE: DNA
<213> ORGANISM: Yarrowia lipolytica

<400> SEQUENCE: 12
agtgagtatt gactggaaag tttgcacaag ttcgcaaaca caagattgag attggtatag 60
gtccaatgtc cactagagcc gatacgagct gtctacaatt gcctgaatag ctcctccatc 120
tcgtcaatcg ttccgcacta acaaagtgct ctcgttaatt gccatctttc tacttgtcac 180
cacggccctc gctcaaacag ccaacatcac gcagtcgacc tacgacttcg ttctcaagta 240

```
cggacgactc tccaatgtgg cctattgtgt caaggccccc ggtccatacg aactggagac    300

ggacttcacc tgtggaagat cttgcggtca ctttcccaac gtgacgttgg aacaccagtt    360

tggaggcgac tttttctcca cgtccataac cggctttctg gcccacgatc acactaagaa    420

agagaaatac attgttttcc gaggcacctt ttctctggca gacgccatca ccgacgcctt    480

gtttctccag gagccctacc tggccgatct gccgcctctg aacaccacca acatcaactc    540

cactagcaat tcggcccgag tcgactgccc cgattgtgag attcatgacg gcttccaaaa    600

ggcataccga gagaccatgg tgaacatgca gggccacctg gtggcctttc ttagaaacaa    660

cacagactac aagctgatag tcaccggcca ttctctggga gccgccactg ctctgctcat    720

gggcatcaac ctgaagaatc tcggctttga ccctatggtg atcacgtttg gacagcctcg    780

agtgggaaac aaggcgtttg cggactacgc cgactcgctc tttttcaaac agggagataa    840

cggactgaat atcaaccctg aaagacgtct ttaccgagtc actcattgga atgacatcgt    900

ggtgggagtg cccttctggt ccggttatac ccatactctg ggagaagtgt acatcagcta    960

cccagacgga gtcaacgccc ccatcgaata cgtcaatgcg tgcgctggac cagacaacga   1020

ccagtgccac tacgggtcct tcgacctgct ggctcgagtc aacattctca aaaaccactg   1080

tgcctatctc aactggatct tctactgcgc ctttaacgtg gacaagagac agatgatgat   1140

tgatcctccg agaatccaca agagagtcga gcattggagc ggcaagtttg cagacgtcga   1200

gttcagcgag agaatgatct acgaggccac ttatcccatg tga                     1243
```

```
<210> SEQ ID NO 13
<211> LENGTH: 363
<212> TYPE: PRT
<213> ORGANISM: Yarrowia lipolytica

<400> SEQUENCE: 13

Met Leu Ser Phe Ile Ala Leu Phe Leu Leu Val Ala Gln Ala Leu Ala
1               5                   10                  15

Gln Thr Ala Pro Ile Thr Gln Glu Thr Tyr Asp Phe Val Leu Lys Tyr
            20                  25                  30

Gly Trp Leu Ser Asn Val Ala Tyr Cys Val Arg Ala Pro Gly Pro Phe
        35                  40                  45

Ala Leu Gln Ser Asp Phe Thr Cys Gly Asn Ser Cys Ala His Phe Pro
    50                  55                  60

Asp Val Thr Leu Asp Tyr Gln Phe Gly Gly Asn Phe Phe Ser Thr Ser
65                  70                  75                  80

Val Thr Gly Phe Leu Ala His Asp His Thr Lys Lys Glu Lys Tyr Ile
                85                  90                  95

Val Phe Arg Gly Thr Phe Ser Ile Ala Asp Ala Ile Thr Asp Ile Gln
            100                 105                 110

Thr Ile Gln Gln Pro Tyr Met Thr Ser Ile Pro Pro Leu Asn Thr Thr
        115                 120                 125

Asp Ile Asn Ser Thr Asn Pro Ser Ala Ser Ile Asn Cys Pro Gly Cys
    130                 135                 140

Gln Val His Asp Gly Phe Gln Lys Ala Tyr Arg Glu Thr Met Val Asn
145                 150                 155                 160

Val Gln Asp Arg Leu Val Asp Phe Leu Gly Asn Asn Thr Asp Tyr Lys
                165                 170                 175

Leu Ile Val Thr Gly His Ser Leu Gly Ala Val Thr Ala Leu Phe Met
            180                 185                 190

Gly Ile Asn Leu Lys Asn Leu Gly Tyr Asp Pro Thr Leu Ile Asn Tyr
```

```
        195                 200                 205

Gly Gln Pro Arg Leu Gly Asn Lys Ala Phe Ala Asp Tyr Val Asp Ala
    210                 215                 220

Leu Phe Phe Lys Gln Gly Asp Asp Gly Leu Thr Ile Asn Pro Glu Arg
225                 230                 235                 240

Arg Met Tyr Arg Val Thr His Trp Asn Asp Phe Phe Val Gly Trp Pro
                245                 250                 255

Ala Gly Tyr Ser His Thr Leu Gly Glu Val Tyr Ile Ser Asp Pro Thr
            260                 265                 270

Gly Ile Asn Ala Pro Ile Glu Asp Val Tyr Ser Cys Ala Gly Pro Glu
        275                 280                 285

Asn Asn Gln Cys His His Gly Ser Phe Asn Leu Leu Glu Arg Leu Asn
    290                 295                 300

Ile Leu Lys Asn His Cys Gly Tyr Leu Asn Trp Ile Phe Tyr Cys Ala
305                 310                 315                 320

Ile Asn Val Asp Lys Arg Glu Met Met Ile Asp Pro Pro Arg Val Gly
                325                 330                 335

Lys Arg Val Glu His Trp Ser Gly Lys Phe Ser Asp Val Glu Ser Thr
            340                 345                 350

Glu Gly Leu Met Tyr Glu Ala Ile Tyr Pro Met
        355                 360


<210> SEQ ID NO 14
<211> LENGTH: 1351
<212> TYPE: DNA
<213> ORGANISM: Yarrowia lipolytica

<400> SEQUENCE: 14

agtgagtatg gagagatgga ctggacttcc atcatcgaga agatgtcaca ggattgtctg     60

ttggcaggaa gtctacagct agttgtggta cagtaccatt ggaagtggcg gtggactatt    120

aagagttgaa gttgttgatg tttctgagaa tgcttatcga tcttggaaac gttcaccact    180

gtcagcttat gctcagaaca actcaatgac aacctttcca actcagtacc tcagttaatt    240

atctcctttg ctaatttcag tgctctcgtt cattgccctc tttcttcttg ttgctcaggc    300

tctcgcgcaa acggctccta tcacccagga gacatacgac tttgttctca agtacggatg    360

gctatctaac gtggcctatt gtgtcagagc ccctggccca tttgccctgc agagcgattt    420

tacctgtgga aactcttgcg ctcattttcc cgatgtgact cttgactacc agtttggagg    480

aaatttcttc tcgacttcag ttactggatt tttggcccac gatcacacca aaaaggaaaa    540

gtatattgtt ttccgaggca ctttctccat tgcagacgct attactgaca tccaaacgat    600

ccaacaaccc tacatgacca gtatccctcc tcttaacact actgacataa actccacaaa    660

cccttctgcc agtatcaatt gtcctggctg ccaagttcat gatggctttc agaaggcata    720

cagagagact atggtgaacg tacaggatcg tctggtcgac ttccttggaa acaacactga    780

ctacaaattg atcgtaactg gccactctct aggagctgtc actgctctat tcatgggcat    840

caacctgaag aatcttggat atgatccaac gctaatcaac tatgggcagc ctcgacttgg    900

aaacaaggct tttgcagact acgtggacgc tctgttcttt aagcaaggag acgacggact    960

taccatcaac cccgaaagac ggatgtaccg agtcactcac tggaacgact tctttgttgg   1020

atggcccgct ggttattcac atactctggg agaagtttac atcagtgatc ccacaggtat   1080

taatgctcct attgaagatg tctattcctg cgctggacca gagaataatc agtgtcacca   1140

tggatcattc aatcttctag aacgactcaa cattctcaag aaccattgcg gttatctcaa   1200
```

```
ttggatttc tactgtgcta tcaatgtgga caagagagag atgatgattg atcctccccg   1260

agttggcaag agagttgagc attggagtgg caagttttct gatgttgaat cgacagaagg   1320

cctgatgtat gaggccattt atcctatgta a                                 1351


<210> SEQ ID NO 15
<211> LENGTH: 376
<212> TYPE: PRT
<213> ORGANISM: Yarrowia lipolytica

<400> SEQUENCE: 15

Met Ile Val Leu Leu Leu Leu Leu Ser Val Ala Leu Ser Ser Pro Ile
1               5                   10                  15

Met Leu Asp Arg Phe Gly Asp Ser Val Asn Arg Met Ile Arg Gly Asn
            20                  25                  30

Ser Glu Ala Tyr Glu Ser Gly Glu Thr Arg Gly Val Ser Gln Glu Phe
        35                  40                  45

Glu Gln Arg Leu Val Arg Tyr Met Trp Phe Asn Asn Val Ala Pro Cys
    50                  55                  60

Val Pro Lys Lys Leu Gln His Pro Phe Lys Cys Ile Ala Arg Gly Cys
65                  70                  75                  80

Lys Glu Leu Gly Lys His Thr Glu Leu Val Asp Ile Phe Thr His Ser
                85                  90                  95

Asp Asn Leu Phe Asp Arg Thr Ile Ser Gly Phe Val Ala Leu Asp His
            100                 105                 110

Lys His Lys Glu Ile Val Leu Ala Leu Arg Gly Thr Gln Asp Ala His
        115                 120                 125

Asp Trp Val Thr Asp Leu His Leu Arg Leu Val Gly Leu His Pro Glu
    130                 135                 140

His Leu Gly Val Ser Asn Phe Asn Cys Arg Asn Cys Gln Val Asp Leu
145                 150                 155                 160

Gly Phe Leu Lys Gly Tyr Leu His Ser Phe His Val Val Asp Ser Ile
                165                 170                 175

Val Gln Arg Leu Thr Glu Lys Tyr Pro Asp Tyr Gln Leu Val Ile Thr
            180                 185                 190

Gly His Ser Leu Gly Gly Thr Ala Ala Thr Leu Phe Gly Leu Asn Tyr
        195                 200                 205

Arg Leu Asn Gly Tyr Ser Pro Leu Val Phe Ser Ala Gly Ala Pro Ala
    210                 215                 220

Leu Gly Asn Lys Gln Phe Ala Asn Phe Ala Asp Arg Val Phe Trp Gly
225                 230                 235                 240

Ser Gln Asn Pro Asn Thr Leu Lys Val Lys Glu Arg Asp Ile Lys Phe
                245                 250                 255

Cys Arg Met Thr His Leu Gly Asp Phe Val Pro Arg Phe Pro Phe Trp
            260                 265                 270

Asn Gly Tyr Gln Gln Met Ser Gly Glu Val Phe Ile Asn Asp Val Arg
        275                 280                 285

Gly Ile Tyr Pro Pro Arg Glu Thr Leu Gln Arg Cys Asn Gly Gln Gln
    290                 295                 300

Asn Arg Gln Cys Ser Phe Gly Asp Gln Tyr Arg Lys Leu Glu Met Asn
305                 310                 315                 320

Phe Lys Pro His Ser Ala Tyr Leu Val Pro Gly Ser Glu Cys Ser Leu
                325                 330                 335

Ser Gly Arg Arg Glu Leu Thr Phe Gly Gln Val His Ala Ala Asn Asp
```

340 345 350

Thr Asn Lys Asp Ser Asp Thr Asn Ile Glu Pro Asp Ile Glu Pro Ile
355 360 365

Leu Ile Pro Val Val Gln Ile Asp
370 375

<210> SEQ ID NO 16
<211> LENGTH: 1131
<212> TYPE: DNA
<213> ORGANISM: Yarrowia lipolytica

<400> SEQUENCE: 16
atgattgttc tacttcttct tctctctgtc gcgttaagta gtccaattat gttggaccgg 60
tttggcgata gtgtgaaccg catgatacga ggcaacagtg aggcgtatga gagcggcgag 120
acacgcgggg tgtcccagga gtttgaacag cggctcgtgc ggtacatgtg gttcaacaat 180
gtggctccat gtgtccccaa gaaacttcag catccattca agtgcatagc tagaggctgc 240
aaagagctgg ggaaacatac agagttggtc gacattttca ctcattcaga caacttgttt 300
gatcgcacaa tttcaggatt tgtggctttg gatcacaagc acaaggagat tgttctggcg 360
ttgagaggca ctcaggatgc ccacgactgg gtgacagacc tgcatctgag gctagtgggg 420
cttcatcccg agcatctggg tgtatcaaac ttcaactgtc gcaactgcca ggtagacctg 480
ggctttctca agggatattt gcattcgttc catgttgttg acagtattgt tcagcgtctg 540
actgaaaaat accccgacta ccaactggtg attacgggcc attcacttgg aggcactgca 600
gctacgctct ttggactcaa ctaccgactc aacggctatt ctcccctagt tttttcggct 660
ggagctccgg cactgggaaa caagcagttt gccaactttg ccgaccgagt cttctgggga 720
tcgcagaacc ccaacactct caaggtcaag gagagagata tcaagttctg tcgcatgacc 780
catctgggtg actttgtgcc tcggtttccc ttctggaacg ggtaccagca aatgtctgga 840
gaggtattta tcaacgacgt gcgaggtata tatccaccca gggagacact ccagcgatgc 900
aacgggcaac agaatagaca gtgctcgttc ggagaccagt accgcaagct ggaaatgaac 960
ttcaagcccc actcggcgta cttggtgcct ggaagcgagt gttcgctcag tggtaggaga 1020
gagttgacat tcggacaagt tcatgcagcg aatgacacaa acaaggactc agacacaaac 1080
attgagcctg acattgaacc aatcttgata cctgtcgtgc aaatagacta a 1131

<210> SEQ ID NO 17
<211> LENGTH: 14006
<212> TYPE: DNA
<213> ORGANISM: Artificial Sequence
<220> FEATURE:
<223> OTHER INFORMATION: plasmid containing expression systems for
DrBCO, LmATF-S480Q_G409A_V407I_H69A_I484L, and FfRDH

<400> SEQUENCE: 17
gcggagccta ggccggccag cgtggcgcgt ggccatattg gccagcagct tactacagct 60
cagccaaagt ggatcatgat ggacggaaat atcggactgg aggccaaaaa ggaggtgctc 120
aaatacgcac gggacaagtc tgcacaggtg gcattcgaac ccacgtctgt ccccaaagcc 180
gctgctcttt ccgagctcaa tctgcccgtt taccccaaca actccattgc cttagccacc 240
cccaacactg cagagctcga ggccatgttc gaggcattcc acgagaaggg ccgatttgac 300
gttgacgact ggtttccagt catagacggt cttgctctcg gagctgactt tagaaacgga 360
gccaccatgt tgtcgcacca acatcgtgga ctcaaagcta ttctcgaaca aggaactctg 420

```
gcccaggcaa tccacatgct accatacatc ccaactttga tcatcaaggg cggagccaac    480
ggcgtcgtcg tcttccaact cattgatgat atcgagtctg ccattcattc acagcgttct    540
gcttccaata aaacgcctgg cctgttccag aagggcaacg ctgcgagtgg aaacaccaag    600
gtcggcgtct acatgcagta ctttgagccc gaagaagtgg gcagtcagtc gattgtaagc    660
gtgactggag ctggagacac tctgtttgga accctggcca tggagattgt caaggacgag    720
tcctggttga acgatatggg agacaagaag agtgcagttg tttctcgagc catgaacaat    780
gctgtgaaga ctattcagag taaggacgct gtctgcaaga gcatccttta agtgatttgc    840
catgctttct cttcttccac gatgtaaata cttattttac acactactgt gcagtagcaa    900
atacagaaca agagttgtcg cctattgaca gtacagtacg agtagtgtat gtacagtagt    960
tatacaatat ctatgtgaaa ttcgtcggca gctttcggct gatgaactac gagttcttcg   1020
taataaatca tcaacgtaat aagcttggta ccagagacgg gttggcggcg tatttgtgtc   1080
ccaaaaaaca gccccaattg ccccaattga ccccaaattg acccagtagc gggcccaacc   1140
ccggcgagag ccccccttcac cccacatatc aaacctcccc cggttcccac acttgccgtt   1200
aagggcgtag ggtactgcag tctggaatct acgcttgttc agactttgta ctagtttctt   1260
tgtctggcca tccgggtaac ccatgccgga cgcaaaatag actactgaaa atttttttgc   1320
tttgtggttg ggactttagc caagggtata aaagaccacc gtccccgaat tacctttcct   1380
cttcttttct ctctctcctt gtcaactcac acccgaaatc gttaagcatt tccttctgag   1440
tataagaatc attcgctagc cacaaaaatg ggtgatctcg atgcccgagg aacctctgct   1500
caccccgagc tctctgagcg accttctatt atgccttcta tgtctgatat tcaggaccct   1560
tctggtgatg acaaggctac tccccgagga tctgctgctg gtctgcccca gcttgagctt   1620
gctggacacg cccgacgact tggccacctt gagaacttct ttgctgtcca ggctcgacag   1680
cagatttact cttcttttgc tgttttttgt gagtttgaca ctgcttgttc tctcgctcag   1740
cttgcttctg ctgtgcgaaa cgtttgtctt tctaaccccc ttctccttca cactgttgag   1800
cctaagcacc ctgacatcgc tggattctac cactctgacg agtaccttc ccgaccttgg   1860
cctcagcacg attacatgcg agttcttcga gaggttcacg tcgctgacgt tgttatgaac   1920
ggacagaagg agcacgctca cgttgttcga gatgctgttg acgtttttca ggctcacgga   1980
aaccaggtta cttctgagct ccttgagctt atgactcaga ttgagattcc tcacgcttct   2040
cagactcgac cctcttggcg acttctctgt tttccccacg gagaggctaa ccgatggcga   2100
acctttgctt ttgtttctaa ccactgttct tctgatggtc tttctggtct taacttcttt   2160
cgagatctcc agaaggagct tgctcacggc cccacctctg gtgctcctgg tgcccccgga   2220
gcttccggag ttattttcga ttacgctcag gacgctgcta ccctgcccaa gctgcccccct   2280
cccattgatc agaagctcga ttaccgacct tctaagaagg ctcttctcgg ccttctcgct   2340
ggcaagttcg ttcgagagaa gctcggttac gtttctgctg ctcctcccac taccccctacc   2400
tctgaccttg ctcaccctga gggtcaccag tactactgtt accttgttaa cgttcccact   2460
tcttctgttg cccacattaa gactcaggtg cgagagaacg ttcctcacaa gtgtactctc   2520
actccctttc tccaggcttg ttggcttgtt tctctgttca agtacggtcg agttttttct   2580
ggttcttggc ttgagcgata caccgatgtt cttgttgcta tgaacactcg acagcttctc   2640
cccgaggacc ttgagcttca gcgacagtac cgatacggtt ctaacattgg agctgttcga   2700
tacaactacc ctattgctcc ccttgacgtt cgagataacg atcagaagtt ctggtccctt   2760
gttgagtctt accgacttgc cctttctgat gcccgagata agaacgatta cctttacgct   2820
```

```
cttggtgctc ttatgctccc tgagatttac gagaagaaga acgttgatgc tgttgttaac   2880
gataccattc ttaaccagcg acgacaggga acccttcttt ctaacgttgg ttacgttcga   2940
gatgagcagc ccactgcttt tgctattaag aaccacgttt tttctcaggg agttggagct   3000
aaccgaaacg cttttgttct taacatttgt gctaccgatc agggtggtct taacatcgct   3060
atttctattg ctaagggaac ccttgcttct cgacaggagg gacaggagct ttgtgatatt   3120
tttaagtcta ctctccttcg attttaaacg cgtctatccg aagatcaaga gcgaagcaag   3180
ttgtaagtcc aggacatgtt tcccgcccac gcgagtgatt tataacacct ctctttttg    3240
acacccgctc gccttgaaat tcatgtcaca taaattatag tcaacgacgt ttgaataact   3300
tgtcttgtag ttcgatgatg atcatatgat tacattaata gtaattactg tatctgtacc   3360
tgctgtggac cacgcacggc ggaacgtacc gtacaaatat tttcttgctc acatgactct   3420
ctctcggccg cgcacgccgg tggcaaattg ctcttgcatt ggctctgtct ctagacgtcc   3480
aaaccgtcca aagtggcagg gtgacgtgat gcgacgcacg aaggagatgg cccggtggcg   3540
aggaaccgga cacggcgagc cggcgggaaa aaaggcggaa aacgaaaagc gaagggcaca   3600
atctgacggt gcggctgcca ccaacccaag gaggctattt tgggtcgctt tccatttcac   3660
attcgccctc aatggccact ttgcggtggt gaacatggtt tctgaaacaa ccccccagaa   3720
ttagagtata ttgatgtgtt taagattggg ttgctatttg gccattgtgg gggagggtag   3780
cgacgtggag gacattccag ggcgaattga gcctagaaag tggtaccatt ccaaccgtct   3840
cagtcgtccg aattgatcgc tataactatc acctctctca catgtctact tccccaacca   3900
acatccccaa cctcccccac actaaagttc acgccaataa tgtaggcact ctttctgggt   3960
gtgggacagc agagcaatac ggaggggaga ttacacaacg agccacaatt ggggagatgg   4020
tagccatctc actcgacccg tcgacttttg gcaacgctca attacccacc aaatttgggc   4080
tggagttgag gggaccgtgt tccagcgctg taggaccagc aacacacacg gtatcaacag   4140
caaccaacgc cccgctaat gcacccagta ctgcgcaggt gtgggccagg tgcgttccag    4200
atgcgagttg gcgaacccta agccgacagt gtacttttg ggacgggcag tagcaatcgt    4260
gggcgtagac cccggtgtat ataaaggggt ggagaggacg gattattagc accaacacac   4320
acacttatac tacatgctag ccacaaaaat gctctctttc ttctggcgaa acggtatcga   4380
gactcccgag cccctcaagg ctgacgtttc cggctctatc cctccctggc ttcagggaac   4440
ccttctccga aacggtcctg gtctgttctc cgttggcaac acttcctaca agcactggtt   4500
cgatggtatg gctctcattc actccttcac ctttaaggat ggtgaggttt tttaccgatc   4560
taagtacctg aagtctgaga cttacaagaa gaacatcgct gccgaccgaa tcgttgtgtc   4620
tgagttcgga accatggtgt accccgatcc ctgcaagaac attttctccc gagccttctc   4680
ttacatgatg aacgccattc ctgactttac cgataacaac ctcattaaca tcattaagta   4740
cggtgaggat tactacgcct cctctgaggt caactacatc aaccagattg accccctgac   4800
ccttgagact ctcggacgaa ctaactaccg aaaccacatt gccatcaacc ttgccactgc   4860
tcaccctcac tacgacgagg agggtaacac ttacaacatg ggcactgcta ttatgaacct   4920
cggtcgaccc aagtacgtga ttttcaaggt gcccgccaac acctctgata aggagaacaa   4980
gaagcctgcc ctctctgagg tggagcaggt ttgctccatt cccatccgac cctcccttta   5040
cccttcttac ttccactctt ttggcatgac tgagaactac atcatcttcg ttgagcaggc   5100
cttcaagctg gacatcgtca agctggctac tgcttacttc cgagatatta actggggatc   5160
```

ttgccttaag ttcgaccagg atgacattaa cgtgttccac ctggtcaaca agaagactgg 5220
taaggctgtg tccgtgaagt actacactga cccctttgtt accttccacc acatcaacgc 5280
ttacgaggac gatggccacg tcgtcttcga tctcattact tacaaggact ctaagctgta 5340
cgatatgttc tacattcaga acatgaagca ggacgtcaag cgatttattg agactaacaa 5400
ggacttcgct cagcccgtgt gccagcgatt tgtccttccc gtcaacgttg ataaggagac 5460
tcctcaggac atcaaccttg tcaagctgca ggacaccact gccactgctg tcctgaagga 5520
ggacggctct gtctactgca cccctgacat catttttaag ggtcttgagc tccctgctat 5580
caactacaag tttaactcta agaagaaccg atacttctac ggcacccgag tggagtggtc 5640
cccttaccct aacaaggtcg ctaaggtgga cgttgttact cgaacccaca agatttggac 5700
tgaggaggag tgttaccctt ctgagcctgt ctttattgcc tcccctgacg ccgttgatga 5760
ggatgacggt gtgattcttt cttctgtggt ttctttcaac ccccagcgac cccctttcct 5820
ggttgtcctc gatgctaagt ccttcaagga gattgctcga gctaccatcg atgcctctat 5880
tcacatggac cttcacggcc ttttcatcca cgacaagtct acctaagttt tttgatcaat 5940
gatccaatgg ctttcacata cccccccacg cctataatta aaacacagag aaatataatc 6000
taacttaata aatattacgg agaatctttc gagtgttcag cagaaatata gccattgtaa 6060
caaaagccgg ctatcgaccg ctttatcgaa gaatatttcc cgcccccag tggccaaacg 6120
atatcggtca gaaggggcag ctctaaacga agaactgcgg tcaggtgaca caactttttc 6180
catctcaggg tgtgtcgcgt gtgcttcatc caaactttag ttggggttcg ggttcgcgcg 6240
agatgatcac gtgccctgat ttggtgtcgt cccccgtcgc gctgcgcacg tgatttattt 6300
atttccggtg gctgctgtct acgcggggcc ttctctgccc ttctgtttca accttcgggc 6360
ggttctcgta accagcagta gcaatccatt tcgaaactca aagagctaaa aacgttaaac 6420
ctcagcagtc gctcgacgaa tgggctgcgg ttgggaagcc cacgaggcct atagccagag 6480
cctcgagttg acaggagccc agacgccttt tccaacggca acttttatat aaaatggcaa 6540
tgtattcatg caattgcggc cgtgtcaggt tggagacact ggaccacact ctccattgct 6600
tcctgaggag atggatcatt gctagtgcat ctacgcgcag caatcccgca agctcgacaa 6660
ccgtagatgg gctttggtgg gccaatcaat tacgcaaccc gcacgttaaa ttgtatgagg 6720
aaggaaggcc acggtacaaa gtgggtggtc ttcacccagt ggttgttggt ggcgtcatgc 6780
agaccatgca ttggggatag cacagggttg gggtgtcttg tggactcaat gggtgaaagg 6840
agatggaaaa gggcggtgaa aagtggtaga atcgaaatcc ctgacgtcaa tttataaagt 6900
aaaatgcgtt tctgccattt tgctcccctc cttctttcgc aatcgcctcc ccaaaagttg 6960
tcgtggcagt acacatgctt gcatacaatg aagctaatcc ggcttgctca gtagttgcta 7020
tatccaggca tggtgtgaaa cccctcaaag tatatatagg agcggtgagc cccagtctgg 7080
ggtcttttct ctccatctca aaactacttt ctcacatgct agccacaaaa atgaccacta 7140
agtacacttc cgttcacgag tctcccaacg gccctggtga cgctcgaccc accgcttccc 7200
agattatcga cgattacaac cttgagggag agctttctgg caagactgtt ctcgtcaccg 7260
gctgttcctc tggtattggt gttgagactg cccgagctat ttaccgaact ggtgccaccc 7320
tttacctcac tgcccgagat gtcgataagg ccaagaccgt tcttcccgac cttgttgaca 7380
cttcccgagt ccactttctc caccttgacc ttaactctct ggagtctgtt cgaggttttg 7440
ctgagaactt caagtctaag tccactcagc ttcacattct catcgagaac gctggcgtga 7500
tggcctgtcc cgagggccga accgtcgatg gttttgagac tcagtttggt atcaaccacc 7560

```
ttgctcactt tctcctcttt tacctcctca aggataccct tctcaactct tctacccccg   7620
ctttcaactc ccgagttgtc atcctctctt cttgtgctca ccaggctggt tccgttcacc   7680
ttaacaacct gtctcttgag ggtggatacg agccttggaa gtcttacggc cagtccaaga   7740
ctgccaacct ttggactgcc cgagagatcg agaagcgatt tggtgcttcc ggtatccact   7800
cttgggctgt tcaccccggt tccatcgcta ctgagcttca gcgacacgtt tccgacgagc   7860
ttaagcagaa gtgggctgac gataaggagg gtgccaagct gtggaagtcc accgagcagg   7920
gtgccgccac cactgtcctt gctgctgttt cccctgagct tgagggtaag ggcggtcttt   7980
accttgagga tacccaggtt gccaagcccc ctgcccgagg aatgtttggt gttgctgact   8040
gggcttacga tgaggatggc ccctctaagc tctgggccaa gtctcttgag ctccttaagc   8100
tccagtaaag gttagactat ggatatgtaa tttaactgtg tatatagaga gcgtgcaagt   8160
atggagcgct tgttcagctt gtatgatggt cagacgacct gtctgatcga gtatgtatga   8220
tactgcacaa cctgtgtatc cgcatgatct gtccaatggg gcatgttgtt gtgtttctcg   8280
atacggagat gctgggtaca agtagctaat acgattgaac tacttatact tatatgaggc   8340
ttgaagaaag ctgacttgtg tatgacttat tctcaactac atccccagtc acaataccac   8400
cactgcacta ccactacaca ctagtggtgt gttctgtgga gcattctcac ttttggtaaa   8460
cgacattgct tcaagtgcag cggaatcaaa aagtataaag tgggcagcga gtatacctgt   8520
acagactgta ggcgataact caatccaatt accccccaca acatgactgg ccaaactgat   8580
ctcaagactt tattgaaatc agcaacaccg attctcaatg aaggcacata cttcttctgc   8640
aacattcact tgacgcctaa agttggtgag aaatggaccg acaagacata ttctgctatc   8700
cacggactgt tgcctgtgtc ggtggctaca atacgtgagt cagaagggct gacggtggtg   8760
gttcccaagg aaaaggtcga cgagtatctg tctgactcgt cattgccgcc tttggagtac   8820
gactccaact atgagtgtgc ttggatcact ttgacgatac attcttcgtt ggaggctgtg   8880
ggtctgacag ctgcgttttc ggcgcggttg gccgacaaca atatcagctg caacgtcatt   8940
gctggctttc atcatgatca catttttgtc ggcaaaggcg acgcccagag agccattgac   9000
gttctttcta atttggaccg atagccgtat agtccagtct atctataagt tcaactaact   9060
cgtaactatt accataacat atacttcact gccccagata aggttccgat aaaaagttct   9120
gcagactaaa tttatttcag tctcctcttc accaccaaaa tgccctccta cgaagctcga   9180
gctaacgtcc acaagtccgc ctttgccgct cgagtgctca agctcgtggc agccaagaaa   9240
accaacctgt gtgcttctct ggatgttacc accaccaagg agctcattga gcttgccgat   9300
aaggtcggac cttatgtgtg catgatcaag acccatatcg acatcattga cgacttcacc   9360
tacgccggca ctgtgctccc cctcaaggaa cttgctctta agcacggttt cttcctgttc   9420
gaggacagaa agttcgcaga tattggcaac actgtcaagc accagtacaa gaacggtgtc   9480
taccgaatcg ccgagtggtc cgatatcacc aacgcccacg gtgtacccgg aaccggaatc   9540
attgctggcc tgcgagctgg tgccgaggaa actgtctctg aacagaagaa ggaggacgtc   9600
tctgactacg agaactccca gtacaaggag ttcctggtcc cctctcccaa cgagaagctg   9660
gccagaggtc tgctcatgct ggccgagctg tcttgcaagg gctctctggc cactggcgag   9720
tactccaagc agaccattga gcttgcccga tccgaccccg agtttgtggt tggcttcatt   9780
gcccagaacc gacctaaggg cgactctgag gactggctta ttctgacccc cggggtgggt   9840
cttgacgaca agggagacgc tctcggacag cagtaccgaa ctgttgagga tgtcatgtct   9900
```

-continued

```
accggaacgg atatcataat tgtcggccga ggtctgtacg gccagaaccg agatcctatt   9960
gaggaggcca agcgatacca gaaggctggc tgggaggctt accagaagat taactgttag  10020
aggttagact atggatatgt aatttaactg tgtatataga gagcgtgcaa gtatggagcg  10080
cttgttcagc ttgtatgatg gtcagacgac ctgtctgatc gagtatgtat gatactgcac  10140
aacctgtgta tccgcatgat ctgtccaatg gggcatgttg ttgtgtttct cgatacggag  10200
atgctgggta caagtagcta atacgattga actacttata cttatatgag gcttgaagaa  10260
agctgacttg tgtatgactt attctcaact acatccccag tcacaatacc accactgcac  10320
taccactaca cctcgagcat gcacactatt atcacattac tacatccaaa cccctacagg  10380
gggaggagct ctccaatcaa atatgtacat taactatctc tcgtaaatca ttgttataag  10440
accgtccgtg actgtctaaa tcggttcatt cgttgtaaca aatcagtgta acaactcgtg  10500
gtacgcccgg tttgcttcgc tcacgctccc ctagattttc cgtctaggac acaacaagcc  10560
ctggtggatg acgttcaacg ccttcagcgc gtctttttcc tcaataacac acgagatgtt  10620
aatttcgttg gctccctgag aaatcatctc aatgttaata cctgcctggg ccagagtaga  10680
gaagaacatg cctgcacatc cgaccatggc cttcattctc gttccgatca gcgacacaat  10740
ggtcatgcct cgcttcacat ctactgtgcc gtactttcgc agctcctcca cagcctgctt  10800
gaggttggag tcgggagcat ggaaggccat cgacacatgg acctcagaag tggagatgag  10860
atcgacgaca agtttctgct ggtcgagagt agcaaagatc ttgttcaaga agccatgact  10920
cttggttcgc ttattcgaat gaacgttgag aacggtgata ttcgatttgg tagtgacagc  10980
tgtaggcttc ttctcgtcat ctacaggagc agacacctgg ggagtgaatg agccagagga  11040
cagagaagtt agcgagtcgg tggaagaagc cagatcctgg acattgtttt tcgttttcag  11100
gttgcccgag ccgtcagcag atgggtagat gatagttcct cctcccaggg ggtttttccac  11160
gtttttgatt cggataggaa tatgggcctt aatgacctgc tccatggtga aggggtggat  11220
gacttcagat ccgtagtagg tcaactcagc ggcctcctcg gggggtaatga tgggcagcag  11280
acgggcagtg gacacctttc tgggatcggc agtgaagaca ccatcgactt ctttccagat  11340
ctgaagctcc ttggcgtcca gacccacagc caccagagca gcacacagat cggtgtatcc  11400
tcgtccgatc tggcttagga ggcctccctt gacggggcca aagaaaccgg tcaacacggg  11460
caccatgttt cccttgacag gagcagagtc cgtgttagga gagccgggaa gagtgatgat  11520
ctcgcccaga acacgtccga ggtccgaata gaacttggga tcttcggcat tggtggtggt  11580
aactgcgtga gacaggtcaa agtaccgtgc gttaacacca gcgtcccgca taactgcagt  11640
catgtacatg caactgagct tctccccaat ggccatgatg gagtcgagtg ttcgggggga  11700
gatctcagaa atgatttcag cagcagccag gattcgcaac agctggtcgc actcgccgtt  11760
gatgtcggca ttgaggtttt cgagcagttc ggggttcttg acgtcacgct tagcagctgc  11820
aagatggtct tctcggatag actcaatgat ggggttgtag gcgtctgatc cgagaagagc  11880
agagtcagca gcagcaataa gacgggtggt ggttccctcg gccttggtgg cctctagatg  11940
gcctccttgg ccccattcca gctgcattaa tgaatcggcc aacgcgcggg gagaggcggt  12000
ttgcgtattg ggcgctcttc cgcttcctcg ctcactgact cgctgcgctc ggtcgttcgg  12060
ctgcggcgag cggtatcagc tcactcaaag gcggtaatac ggttatccac agaatcaggg  12120
gataacgcag gaaagaacat gtgagcaaaa ggccagcaaa aggccaggaa ccgtaaaaag  12180
gccgcgttgc tggcgttttt ccataggctc cgcccccctg acgagcatca caaaaatcga  12240
cgctcaagtc agaggtggcg aaacccgaca ggactataaa gataccaggc gtttccccct  12300
```

```
ggaagctccc tcgtgcgctc tcctgttccg accctgccgc ttaccggata cctgtccgcc  12360
tttctccctt cgggaagcgt ggcgctttct catagctcac gctgtaggta tctcagttcg  12420
gtgtaggtcg ttcgctccaa gctgggctgt gtgcacgaac cccccgttca gcccgaccgc  12480
tgcgccttat ccggtaacta tcgtcttgag tccaacccgg taagacacga cttatcgcca  12540
ctggcagcag ccactggtaa caggattagc agagcgaggt atgtaggcgg tgctacagag  12600
ttcttgaagt ggtggcctaa ctacggctac actagaagaa cagtatttgg tatctgcgct  12660
ctgctgaagc cagttacctt cggaaaaaga gttggtagct cttgatccgg caaacaaacc  12720
accgctggta gcggtggttt ttttgtttgc aagcagcaga ttacgcgcag aaaaaaagga  12780
tctcaagaag atcctttgat cttttctacg gggtctgacg ctcagtggaa cgaaaactca  12840
cgttaaggga ttttggtcat gagattatca aaaaggatct tcacctagat ccttttaaat  12900
taaaaatgaa gttttaaatc aatctaaagt atatatgagt aaacttggtc tgacagttac  12960
caatgcttaa tcagtgaggc acctatctca gcgatctgtc tatttcgttc atccatagtt  13020
gcctgactcc ccgtcgtgta gataactacg atacgggagg gcttaccatc tggccccagt  13080
gctgcaatga taccgcgaga gccacgctca ccggctccag atttatcagc aataaaccag  13140
ccagccggaa gggccgagcg cagaagtggt cctgcaactt tatccgcctc catccagtct  13200
attaattgtt gccgggaagc tagagtaagt agttcgccag ttaatagttt gcgcaacgtt  13260
gttgccattg ctacaggcat cgtggtgtca cgctcgtcgt ttggtatggc ttcattcagc  13320
tccggttccc aacgatcaag gcgagttaca tgatccccca tgttgtgcaa aaaagcggtt  13380
agctccttcg gtcctccgat cgttgtcaga agtaagttgg ccgcagtgtt atcactcatg  13440
gttatggcag cactgcataa ttctcttact gtcatgccat ccgtaagatg cttttctgtg  13500
actggtgagt actcaaccaa gtcattctga gaatagtgta tgcggcgacc gagttgctct  13560
tgcccggcgt caatacggga taataccgcg ccacatagca gaactttaaa agtgctcatc  13620
attggaaaac gttcttcggg gcgaaaactc tcaaggatct taccgctgtt gagatccagt  13680
tcgatgtaac ccactcgtgc acccaactga tcttcagcat cttttacttt caccagcgtt  13740
tctgggtgag caaaaacagg aaggcaaaat gccgcaaaaa agggaataag ggcgacacgg  13800
aaatgttgaa tactcatact cttccttttt caatattatt gaagcattta tcagggttat  13860
tgtctcatga gcggatacat atttgaatgt atttagaaaa ataaacaaat aggggttccg  13920
cgcacatttc cccgaaaagt gccacctgac gtctaagaaa ccattattat catgacatta  13980
acctataaaa ataggcgtat cacgag                                     14006
```

<210> SEQ ID NO 18
<211> LENGTH: 559
<212> TYPE: PRT
<213> ORGANISM: Lachancea mirantina

<400> SEQUENCE: 18

```
Met Gly Asp Leu Asp Ala Arg Gly Thr Ser Ala His Pro Glu Leu Ser
1               5                   10                  15

Glu Arg Pro Ser Ile Met Pro Ser Met Ser Asp Ile Gln Asp Pro Ser
            20                  25                  30

Gly Asp Asp Lys Ala Thr Pro Arg Gly Ser Ala Ala Gly Leu Pro Gln
        35                  40                  45

Leu Glu Leu Ala Gly His Ala Arg Arg Leu Gly His Leu Glu Asn Phe
    50                  55                  60
```

-continued

```
Phe Ala Val Gln His Arg Gln Gln Ile Tyr Ser Ser Phe Ala Val Phe
65                  70                  75                  80

Cys Glu Phe Asp Thr Ala Cys Ser Leu Ala Gln Leu Ala Ser Ala Val
                85                  90                  95

Arg Asn Val Cys Leu Ser Asn Pro Leu Leu Leu His Thr Val Glu Pro
            100                 105                 110

Lys His Pro Asp Ile Ala Gly Phe Tyr His Ser Asp Glu Tyr Leu Ser
        115                 120                 125

Arg Pro Trp Pro Gln His Asp Tyr Met Arg Val Leu Arg Glu Val His
    130                 135                 140

Val Ala Asp Val Val Met Asn Gly Gln Lys Glu His Ala His Val Val
145                 150                 155                 160

Arg Asp Ala Val Asp Val Phe Gln Ala His Gly Asn Gln Val Thr Ser
                165                 170                 175

Glu Leu Leu Glu Leu Met Thr Gln Ile Glu Ile Pro His Ala Ser Gln
            180                 185                 190

Thr Arg Pro Ser Trp Arg Leu Leu Cys Phe Pro His Gly Glu Ala Asn
        195                 200                 205

Arg Trp Arg Thr Phe Ala Phe Val Ser Asn His Cys Ser Ser Asp Gly
    210                 215                 220

Leu Ser Gly Leu Asn Phe Phe Arg Asp Leu Gln Lys Glu Leu Ala His
225                 230                 235                 240

Gly Pro Thr Ser Gly Ala Pro Gly Ala Pro Gly Ala Ser Gly Val Ile
                245                 250                 255

Phe Asp Tyr Ala Gln Asp Ala Ala Thr Leu Pro Lys Leu Pro Pro Pro
            260                 265                 270

Ile Asp Gln Lys Leu Asp Tyr Arg Pro Ser Lys Lys Ala Leu Leu Gly
        275                 280                 285

Leu Leu Ala Gly Lys Phe Val Arg Glu Lys Leu Gly Tyr Val Ser Ala
    290                 295                 300

Ala Pro Pro Thr Thr Pro Thr Ser Asp Leu Ala His Pro Glu Gly His
305                 310                 315                 320

Gln Tyr Tyr Cys Tyr Leu Val Asn Val Pro Thr Ser Ser Val Ala His
                325                 330                 335

Ile Lys Thr Gln Val Arg Glu Asn Val Pro His Lys Cys Thr Leu Thr
            340                 345                 350

Pro Phe Leu Gln Ala Cys Trp Leu Val Ser Leu Phe Lys Tyr Gly Arg
        355                 360                 365

Val Phe Ser Gly Ser Trp Leu Glu Arg Tyr Thr Asp Val Leu Val Ala
    370                 375                 380

Met Asn Thr Arg Gln Leu Leu Pro Glu Asp Leu Glu Leu Gln Arg Gln
385                 390                 395                 400

Tyr Arg Tyr Gly Ser Asn Val Gly Gly Val Arg Tyr Asn Tyr Pro Ile
                405                 410                 415

Ala Pro Leu Asp Val Arg Asp Asn Asp Gln Lys Phe Trp Ser Leu Val
            420                 425                 430

Glu Ser Tyr Arg Leu Ala Leu Ser Asp Ala Arg Asp Lys Asn Asp Tyr
        435                 440                 445

Leu Tyr Ala Leu Gly Ala Leu Met Leu Pro Glu Ile Tyr Glu Lys Lys
    450                 455                 460

Asn Val Asp Ala Val Val Asn Asp Thr Ile Leu Asn Gln Arg Arg Ser
465                 470                 475                 480

Gly Thr Leu Ile Ser Asn Val Gly Tyr Val Arg Asp Glu Gln Pro Thr
```

-continued

```
                485                 490                 495

Ala Phe Ala Ile Lys Asn His Val Phe Ser Gln Gly Val Gly Ala Asn
            500                 505                 510

Arg Asn Ala Phe Val Leu Asn Ile Cys Ala Thr Asp Gln Gly Gly Leu
        515                 520                 525

Asn Ile Ala Ile Ser Ile Ala Lys Gly Thr Leu Ala Ser Arg Gln Glu
    530                 535                 540

Gly Gln Glu Leu Cys Asp Ile Phe Lys Ser Thr Leu Leu Arg Phe
545                 550                 555
```

METHOD TO PRODUCE RETINYL ACETATE

This application is the U.S. national phase of International Application No. PCT/EP2021/070909 filed Jul. 27, 2021, the entire contents of which are hereby incorporated by reference.

The present invention is related to a novel process for production of retinyl acetate in a host cell, particularly oleaginous yeast such as e.g. *Yarrowia*, wherein the product purity could be increased with reduction of unwanted side-products. Particularly, the novel process comprises fermentation in the presence of ethanol, such as e.g. in a fed-batch fermentation process. Such process is especially useful in a biotechnological process for production of vitamin A.

Current chemical production methods for retinoids, including vitamin A and precursors thereof, have some undesirable characteristics such as e.g. high-energy consumption, complicated purification steps and/or undesirable by-products. Therefore, over the past decades, other approaches to manufacture retinoids, including vitamin A and precursors thereof, comprising microbial conversion steps have been investigated, which would lead to more economical as well as ecological vitamin A production.

In general, the biological systems that produce retinoids are industrially intractable and/or produce the compounds at such low levels that commercial scale isolation is not practical. The most limiting factors include instability of intermediates in such biological systems and/or the relatively high production of by-products, such as e.g. fatty acid retinyl esters (FAREs), particularly using oleaginous host cells grown on vegetable oils or glucose as carbon source.

Whereas instability could be solved via expression of highly specific acetylating enzymes (ATFs) in the host cell resulting in increased accumulation of retinyl acetate, a relatively high percentage of retinol is still "lost" for vitamin A production, i.e. converted into undesired side-products including FAREs, that are difficult to purify and do not form a crystal, but instead form a wax. Thus, high concentrations of FAREs limit large scale, industrial production of pure products.

Thus, there is a strong need to improve purity and/or productivity in production of retinyl acetate using yeast, particularly oleaginous host cells such as *Yarrowia.*

Surprisingly, we now found that production of retinoids is improved via fermentation in the presence of ethanol, particularly in a fed-batch fermentation process, leading to reduction or abolishment of impurities including FAREs, increase in retinyl acetate and/or total retinoids.

Particularly, the present invention is directed to a process for production of retinyl acetate in a fungal host cell, preferably oleaginous yeast cell such as e.g. *Yarrowia*, comprising cultivation of the host cell in the presence of ethanol added during the fermentation, particularly in a fed-batch fermentation process, wherein the formation of by-products including FAREs is reduced or abolished, preferably reduced by about 50-100% based on total retinoids, compared to fermentation without ethanol, particularly compared to a (fermentation) process in the presence of triglycerides, particularly vegetable oil, as defined herein.

As used herein, the term "by-products" and "side-products" in connection with fermentative production of retinoids that are used interchangeably herein means retinoids generated during the fermentation process, with the exception of retinyl acetate. The formation of by-products which is to be reduced or abolished during the fermentation includes particularly the formation of FARE, optionally furthermore presence of retinol or retinal present in the cultivation medium and which might be purified from the retinyl acetate.

As used herein, a fermentation "in the "presence of ethanol" or "ethanol added during the fermentation" particularly refers to a fed-batch fermentation process, wherein the batch phase comprises a concentration of about 5% ethanol (v/v) or less, such as e.g. an amount of about 5, 4.5, 4, 3.5, 3, 2.5, 2, 1.5, 1% added to the cultivation medium during the batch phase of the fermentation. Ethanol feed is controlled via measurement of the pH and/or DO as known in the art, typically with feeding of about 100% ethanol and with DO setpoint of about 40 to 20% Optionally, either the batch phase or the feed further comprises glucose, such as e.g. an amount of about 20, 15, 10, 8, 5, 3, 2% or less glucose added to the cultivation medium during the batch phase of the fermentation or ratios of ethanol to glucose in the range of about 9:1, 8:2, 7:3.

As used herein, a fermentation "in the "presence of triglycerides, particularly vegetable oil" or "triglycerides, particularly vegetable oil, added during the fermentation" particularly refers to a fed-batch fermentation process, wherein the batch phase comprises a concentration of about 10% triglycerides (v/v) or less, particularly vegetable oil, such as e.g. an amount of about 10, 8, 6, 5, 4, 3, 2, 1% added to the cultivation medium during the batch phase of the fermentation. The oil to be used is particularly vegetable oil, such as e.g. oil originated from corn, soy, olive, sunflower, canola, cottonseed, rapeseed, sesame, safflower, grapeseed or mixtures thereof, including the respective free fatty acids, such as e.g. oleic acid, palmitic acid or linoleic acid.

In one preferred embodiment, the present invention is related to a process as described herein for reducing FARE-production in retinyl acetate production process, wherein the percentage of by-products including FAREs could be reduced by about 100%, i.e. more or less abolished, said process comprising the fermentation in the presence of ethanol as defined herein. Compared to a fermentation process in the presence of triglycerides as defined herein, the formation of FAREs could be reduced by at least about 50%, such as e.g. about 55, 60, 65, 70, 75, 80, 85, 90, 95 or 100%, i.e. abolishment of FARE formation.

Preferably, the present invention is directed to a retinyl acetate production process as defined herein, wherein the production of FARE formed during the fermentation is less than about 25%, such as e.g. less than about 20, 15, 10, 8, 5, 3, 2, 1% based on total retinoids.

Furthermore, the present invention is directed to a process for production of retinyl acetate in a fungal host cell, preferably oleaginous yeast cell such as e.g. *Yarrowia*, said process comprising fermentation in the presence of ethanol as defined herein, wherein the percentage of retinyl acetate formation could be increased by at least about 25%, such as e.g. by about 30, 35, 40, 45, 50, 55, 60, 65, 70, 75, 80, 85, 90, 95, 100% or more based on total retinoids, compared to the respective process in the absence of ethanol, particularly compared to a fermentation process in the presence of triglycerides as defined herein.

Thus, in one particular embodiment, the present invention is related to a process as described herein for production of retinyl acetate in a fungal host cell as defined herein, wherein the percentage of retinyl acetate formed during the fermentation is in the range of at least about 50-80%, such as e.g. a percentage of at least about 50, 55, 60, 65, 70, 75, 80, 85, 87, 90, 95, 98% or up to 100% based on total retinoids, said process comprising the fermentation in the presence of ethanol as defined herein.

In a further aspect, the present invention is directed to a process for increasing total retinoids, with an increase in retinoids in the range of at least about 30%, such as e.g. an increase of about 30, 35, 40, 45, 50, 60, 70, 80% or more, said process comprising the fermentation in the presence of ethanol as defined herein, as compared to the respective process in the absence of ethanol, particularly compared to a fermentation process in the presence of triglycerides as defined herein.

In one embodiment, the present invention is directed to a process as defined herein, wherein a retinyl acetate producing host cell, preferably oleaginous yeast cell such as e.g. *Yarrowia*, is cultivated under suitable culture conditions comprising fermentation in the presence of ethanol as defined herein, wherein the percentage of FAREs formed during the fermentation is in the range of less than 25%, preferably less than about 10%, and the percentage of retinyl acetate is the range of at least about 50-80%, preferably in the range of at least about 70, 80, 85, 87, 90, 95, 98% based on total retinoids. Compared to a process in the absence of ethanol during the fermentation, particularly wherein the host cell is cultivated in a fermentation process in the presence of triglycerides, particularly vegetable oil, as defined herein, the percentage of retinyl acetate might be increased by about 100% or more and the percentage of FAREs might be reduced to a range of about 10 to 1%, or even to less than about 1%, or even abolished, based on total retinoids.

The present invention is directed to the use of a retinyl acetate producing host cell, particularly fungal host cell, preferably oleaginous yeast cell such as e.g. such as e.g. *Rhodosporidium, Lipomyces* or *Yarrowia*, preferably *Yarrowia*, more preferably *Yarrowia lipolytica*, in a process as defined herein, e.g. in a fermentation process comprising addition of ethanol during the fermentation as defined herein, wherein the process is particularly a fed-batch fermentation, wherein the batch phase comprises a concentration of about 5% ethanol (v/v) or less, particularly 2 to 1% (v/v) ethanol in the batch phase. Particularly, suitable host cells are expressing genes coding for heterologous enzymes EC class [EC 2.3.1.84] catalyzing the enzymatic conversion of retinol into retinyl acetate. Suitable strains expressing such ATFs are described in e.g. WO2019058001 or WO2020141168.

Preferably, the host cell to be used in the present invention is expressing a heterologous ATF, particularly fungal ATF, comprising a highly conserved partial amino acid sequence of at least 7 amino acid residues selected from [NDEHCS]H-x (3)-D-[GA] (motifs are in Prosite syntax, as defined in h-t-t-p-s://prosite.expasy.org/scanprosite/scanprosite_doc.html), wherein "x" denotes an arbitrary amino acid and with the central histidine being part of the enzyme's binding pocket, preferably wherein the 7 amino acid motif is selected from [NDE]-H-x (3)-D-[GA], more preferably selected from [ND]-H-x (3)-D-[GA], most preferably selected from N—H-x (3)-D-[GA] corresponding to position N218 to G224 in the polypeptide according to SEQ ID NO: 18. Examples of such enzymes might be particularly selected from *L. mirantina, L. fermentati, S. bayanus*, or *W. anomalus*, such as e.g. LmATF1 according to SEQ ID NO: 18, SbATF1, LffATF1, LfATF1, Wa1ATF1 or Wa3ATF1 as disclosed in WO2019058001, more preferably said ATFs comprising one or more amino acid substitution(s) in a sequence with at least about 20%, such as e.g. 25, 30, 35, 40, 45, 50, 55, 60, 65, 70, 75, 80, 85, 90, 92, 95, 97, 98, 99% or up to 100% identity to SEQ ID NO:18, wherein the one or more amino acid substitution(s) are located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof and as particularly exemplified in Table 4 of WO2020141168, most preferably comprising one or more amino acid substitution(s) on positions corresponding to amino acid residue(s) 69, 407, 409, 480, 484, and combinations thereof in SEQ ID NO: 18.

In one particular embodiment, the host cell to be used for the process according to the present invention comprises an amino acid substitution at a position corresponding to residue 69 in the polypeptide according to SEQ ID NO:18 leading to asparagine, serine or alanine at said residue, such as e.g. via substitution of histidine by asparagine (H69N), serine (H69S) or alanine (H69A), with preference for H69A. Said modified enzyme might be originated from yeast, such as e.g. *L. mirantina, L. fermentati, W. anomalus* or *S. bayanus*, preferably from *L. mirantina*, optionally being combined with amino acid substitution at a position corresponding to residue 407 in the polypeptide according to SEQ ID NO:18 leading to isoleucine at said residue, such as e.g. via substitution of valine by isoleucine (V407I), optionally being combined with an amino acid substitution at a position corresponding to residue 409 in the polypeptide according to SEQ ID NO:18 leading to alanine at said residue, such as e.g. via substitution of glycine by alanine (G409A), optionally being combined with amino acid substitution at a position corresponding to residue 480 in the polypeptide according to SEQ ID NO:18 leading to glutamic acid, lysine, methionine, phenylalanine or glutamine at said residue, such as e.g. via substitution of serine by glutamic acid (S480E), lysine (S480L), methionine (S480M), phenylalanine (S480F) or glutamine (S480Q), optionally being combined with amino acid substitution at a position corresponding to residue 484 in the polypeptide according to SEQ ID NO:18 leading to leucine at said residue, such as e.g. via substitution of isoleucine by leucine (I484L). Said modified enzyme might be originated from yeast, such as e.g. *L. mirantina, L. fermentati, W. anomalus* or *S. bayanus*, preferably from *L. mirantina*. In a most preferred embodiment, the ATF to be used for the process according to the present invention is a modified ATF comprising amino acid substitutions S480Q_G409A_V407I_H69A_I484 L and is obtainable from *Lachancea mirantina.*

As used herein, the term "host cell" includes retinyl-acetate producing cells, i.e. capable of synthesizing retinol and expressing ATF as defined herein resulting in retinyl acetate with a percentage as defined herein based on total retinoids produced by said host cell. Optionally, such host cell is furthermore capable of producing carotenoids. A "fungal host cell" particularly includes yeast cells, i.e. retinyl acetate-producing yeast cells, including but not limited to *Yarrowia, Rhodosporidium*, or *Lipomyces.*

Optionally, the host cell, such as e.g. *Yarrowia*, capable of producing retinyl acetate from conversion of retinol, is expressing further enzymes used for biosynthesis of beta-carotene and/or additionally used for catalyzing conversion of beta-carotene into retinal and/or retinal into retinol. The skilled person knows which genes to be used/expressed for either biosynthesis of beta-carotene and/or bio-conversion of beta-carotene into retinol. Such host cell further being capable of expressing ATF genes as defined herein and/or further genes required for biosynthesis of vitamin A, is cultured in an aqueous medium comprising addition of ethanol during the fermentation, optionally supplemented with appropriate nutrients under aerobic or anaerobic conditions and as known by the skilled person to enable production of retinyl acetate. Preferably, the fermentation is performed in fed-batch, wherein the batch phase comprises a concentration of about 5% or less ethanol, particularly 2 to 1% ethanol, and with feed of 100% ethanol as particularly exemplified herein. Particularly, fermentations are run in fed-batch stirred tank reactors. Fermentations can be run for 5 to 14 days, such as e.g. for around 118 h. Fermentation products including retinyl acetate may be harvested from the cultivation at a suitable moment, e.g. when the tank fills due to addition of the feed. Depending on the host cell, preferably, production of retinoids such as e.g. vitamin A, precursors and/or derivatives thereof such as retinal, retinol, retinyl acetate, particularly retinyl acetate, can vary, as it is known to the skilled person. The retinoids including but not limited to retinol, retinyl acetate, vitamin A might be used as ingredients/formulations in the food, feed, pharma or cosmetic industry. Cultivation and isolation of beta-carotene and retinoid-producing host cells selected from *Saccharomyces* is described in e.g. WO2008042338.

In one embodiment, the host cell to be used for the process according to the present invention might comprise further modifications, such as modification in endogenous enzyme activities leading to conversion of retinol into FAREs. Particularly, such modifications include deletion of endogenous lipase activities, i.e. activities in enzymes involved in pre-digestion of triglyceride oils such as e.g. vegetable oil into glycerol and fatty acids that are normally expressed in oleaginous host cells. Suitable enzymes to be modified in a host cell used in the process as defined herein might be selected from endogenous enzymes belonging to EC class 3.1.1.-, including, but not limited to one or more enzyme(s) with activities corresponding to *Yarrowia* LIP2, LIP3, LIP4, LIP8, TGL1, LIP16, LIP17, or LIP18 activities, preferably reduction or abolishment of endogenous genes encoding enzymes with activities corresponding to *Yarrowia* LIP2 and/or LIP3 and/or LIP4 and/or LIP8 activities.

As used herein, an enzyme having activity corresponding to the respective LIP activity in *Yarrowia* includes not only the genes originating from *Yarrowia*, e.g. *Yarrowia lipolytica*, such as e.g. *Yarrowia* LIP2, LIP3, LIP4, LIP8, TGL-1, LIP16, LIP17, LIP18 or combinations thereof according to SEQ ID NOs:1, 3, 5, 7, 9, 11, 13, 15 but also includes enzymes having equivalent enzymatic activity but are originated from another source organism, particularly retinyl acetate-producing oleaginous host cell. Preferably, the host cell comprises deletion of endogenous lipase activities corresponding to *Yarrowia lipolytica* lipase activities 2, 3, 4, 8, or combinations thereof, in particular wherein the host cell is *Yarrowia lipolytica* comprising deletion of endogenous lipase activities such as lip8 or combinations of lip8, such as combination of lip8 with lip2, combination of lip8 with lip2 and lip3, or combination of lip8 with lip2, lip3, and lip4 activities.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, h-t-t-p://emboss.bioinformatics.nl/). For protein sequences EBLOSUM62 is used for the substitution matrix. For nucleotide sequence, EDNAFU LL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity.

The enzymes as defined herein to be expressed in a suitable host cell to be used in the present invention also encompass enzymes carrying (further) amino acid substitution(s) which do not alter enzyme activity, i.e. which show the same properties with respect to the enzymes defined herein. Such mutations are also called "silent mutations", which do not alter the (enzymatic) activity of the enzymes according to the present invention.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

The present invention is directed to a process for production of retinyl acetate, wherein the retinyl acetate is generated via acetylation of retinol (particularly at least 65% as trans-retinol) as disclosed herein by the action of modified/non-modified ATF as described herein, wherein the acetylating enzymes are heterologous expressed in a suitable host cell under suitable conditions as described herein and wherein the host cell is cultivated in a medium comprising an effective amount of ethanol added during the fermentation. The produced retinyl acetate might be isolated and optionally further purified from the medium and/or host cell. Said acetylated retinoids defined herein can be used as building blocks in a multi-step process leading to vitamin A. Vitamin A might be isolated and optionally further purified from the medium and/or host cell as known in the art.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity. Analytical methods to evaluate the capability of a suitable ATF (wild-type or modified) as defined herein for retinyl acetate production, i.e. acetylation of retinol, or enzymes with lipase activity as defined herein are known in the art, such as e.g. described in Example 4 of WO2014096992. In brief, titers of products such as retinyl acetate, retinol, trans-retinal, cis-retinal, beta-carotene and the like can be measured by HPLC.

With regards to suitable host cells comprising specific enzymes involved in biosynthesis of beta-carotene and that are expressed and active in vivo leading to production of carotenoids, e.g. beta-carotene, both genes and methods to generate carotenoid-producing host cells are known in the art, see e.g. WO2006102342. Depending on the carotenoid to be produced, different genes might be involved.

As used herein, a "retinol-producing host cell" is a host cell, wherein the respective polypeptides are expressed and active in vivo, leading to production of retinoids, e.g. vitamin A and its precursors including retinol, via enzymatic activity of the ATFs as described herein. The genes of the vitamin A pathway and methods to generate retinoid-producing host cells are known in the art. The term retinoid includes retinol, which is used as a substrate for the modified acetylating enzymes as defined herein. A "retinyl acetate-producing host cell" is the respective host cell capable of acetylation of retinol into retinyl acetate.

Retinoids as used herein include beta-carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Biosynthesis of retinoids is described in e.g. WO2008042338.

"Retinal" as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

"Vitamin A" as used herein may be any chemical form of vitamin A found in solutions, in solids and formulations, and includes retinol, retinyl acetate and retinyl esters. It also includes retinoic acid, such as for instance undissociated, in its free acid form or dissociated as an anion.

It was also surprisingly found that the production of other isoprenoid-derived products, such as steviol glycosides, was improved via fermentation of a recombinant fungal host cell, particularly a yeast cell such as e.g. a *Saccharomyces cerevisiae* cell, more particularly an oleaginous yeast cell such as e.g. a recombinant *Yarrowia* cell (suitably modified to be able to produce steviol glycosides), in the presence of ethanol. It was found that the production of said products was increased when ethanol was provided as a carbon source, particularly in a fed-batch fermentation process, when compared to the respective process in the absence of ethanol. More particularly, the production of said products was increased with the use of pure ethanol feeds or mixed ethanol feeds (e.g. ethanol/glucose mixture) following the batch phase of growth.

Accordingly, the present disclosure is directed to a process for the production of steviol glycosides in a recombinant fungal host cell, preferably a yeast cell such as e.g. a *Saccharomyces cerevisiae* cell, more preferably an oleaginous yeast cell such as e.g. a recombinant *Yarrowia* cell, more preferably *Yarrowia lipolytica* (suitably modified to be able to produce steviol glycosides), said process comprising fermentation in the presence of ethanol as defined herein. The present disclosure is also directed to the use of a host cell that produces steviol glycosides, preferably a yeast cell such as e.g. a *Saccharomyces cerevisiae* cell, more preferably an oleaginous yeast cell such as e.g. a recombinant *Yarrowia* cell, more preferably *Yarrowia lipolytica* (suitably modified to be able to produce steviol glycosides), in a fermentation process comprising addition of ethanol during the fermentation as defined herein.

Suitable fungal host cells for the production of steviol glycosides are known in the art and are described in e.g. WO2011153378, WO2013022989, WO2014122227, WO2013110673, and WO2015007748.

The produced steviol glycosides might be isolated and optionally further purified from the medium and/or host cell according to a method known to the skilled person in the art.

The following examples are illustrative only and are not intended to limit the scope of the invention in any way. The contents of all references, patent applications, patents, and published patent applications, cited throughout this application are hereby incorporated by reference, in particular WO2019058001, WO2020141168, WO2008042338, WO2014096992, WO2006102342, WO2016172282, WO2011153378, WO2013022989, WO2014122227, WO2013110673, and WO2015007748.

EXAMPLES

Example 1: General Methods and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

DNA transformation. Strains were transformed by overnight growth on YPD plate media; 50 µl of cells was scraped from a plate and transformed by incubation in 500 µl with 1 µg transforming DNA, typically linear DNA for integrative transformation, 40% PEG 3550MW, 100 mM lithium acetate, 50 mM Dithiothreitol, 5 mM Tris-Cl pH 8.0, 0.5 mM EDTA for 60 minutes at 40° C. and plated directly to selective media or in the case of dominant antibiotic marker selection the cells were out grown on YPD liquid media for 4 hours at 30° C. before plating on the selective media. URA3 marker recycling was performed using 5-fluoroorotic acid (FOA). Episomal hygromycin resistance marker plasmids were cured by passage on non-selective media, with identification of Hyg-sensitive colonies by replica plating colonies from non-selective media to hygromycin containing media (100 µg/mL).

DNA molecular biology. Plasmids MB9523 containing expression systems for DrBCO, LmATF-S480Q_G409A_V407I_H69A_I484 L, and FfRDH (SEQ ID NO:17) was synthesized at Genscript (Piscataway, NJ, USA). Plasmid MB9523 contains the 'URA3' for marker selection in *Yarrowia lipolytica* transformations. For gene insertion by random nonhomologous end joining of the gene and marker, SfiI-digested MB9523 plasmid fragment of interest was purified by gel electrophoresis and Qiagen gel purification column. Clones were verified by sequencing. Typically, genes are synthesized by a synthetic biology at GenScript (Piscataway, NJ).

Plasmid list. Plasmid, strains, nucleotide and amino acid sequences that were used are listed in Table 1, 2 and the sequence listing. In general, all non-modified sequences referred to herein are the same as the accession sequence in the database for reference strain CLIB122 (Dujon B, et al, Nature. 2004 Jul. 1; 430(6995):35-44).

TABLE 1 list of plasmids used for construction of the strains for overexpression or deletion of the respective genes indicated as "insert". "LmATF1-mut" refers to *Lachancea mirantina* (LmATF1; SEQ ID NO: 13 in WO2019058001) carrying aa substitutions S480Q_G409A_V407I_H69A_I484L. "DrBCO" refers to BCO originated from *Danio rerio* (see SEQ ID NO: 16 in WO2020141168); "FfRDH" refers to RDH originated from *Fusarium fujikuroi* (see SEQ ID NO: 22 in WO2020141168). For more explanation, see text.

| Plasmid | Insert | Marker | SEQ ID NO |
|---|---|---|---|
| MB9523 | DrBCO; LmATF1-mut; FfRDH | URA3 | 17 |

TABLE 2 list of *Yarrowia lipolytica* strains used. Construction of ML17544 is described in Table 2 of WO2020141168. For more details, see text.

| Strain | Description |
|---|---|
| ML18812 | ML17544 transformed with MB9523 |

Fermentation conditions. Fed-batch fermentations were identical to the previously described conditions except using Drakeol 5 (Penreco, Karns City, PA, USA) or another overlay and stirred tank that was corn oil, glucose or ethanol fed in a bench top reactor with 0.5 L to 5 L total volume (see WO2016172282). The batch medium carbon source composition and feed medium are listed in Table 3. Feeding was initiated after the initial batch carbon had been consumed, with feed added in a controlled manner to maintain a dissolved oxygen level (DO) setpoint.

Briefly, the fermentations were run in 3.0 L flood volume in glass New Brunswick or Eppendorf fermentation systems. The fermentor was batched with the following components: 2228 mL of deionized water, $MgSO_4 \cdot 7H_2O$ is 1.96 g/kg and NaCl is 0.20 g/kg, 10.46 mL, 1.04 g $CaCl_2$)-$2H_2O$, 26.18 g $(NH_4)2SO_4$, 27.10 g $KH_2PO_4$, 19.62 g Tastone yeast extract (Marcor, Leominster, MA), 26 mL DF204 antifoam, 0.654 µL, thiamine HCl at 4 mg/ml, trace elements stock solution 3.27 ml/L 20) containing: 200 g/kg citric acid, 27.3 g/kg $FeSO_4 \cdot 7H_2O$, 19.6 g/kg $Na_2MoO_4 \cdot 2H_2O$, 18.7 $CuSO_4 \cdot 5H_2O$, 4.9 $H_3BO_3$, 21.9 $MnSO_4 \cdot H_2O$, 30.2 $ZnSO_4 \cdot 7H_2O$, and autoclaved. After cooling a carbon source was added along with 800 mL Drakeol 5 or other second phase. The fermentation was inoculated with 200 ml overnight shake flask cultures of YP media grown with 250 RPM agitation at 30° C. and the specific carbon sources shown in Table 3. Fermentation parameters were agitation at 1000 RPM, airflow at 4.6 LPM for ethanol and 2.3 LPM for oil and mixed fatty acids, pH controlled at 5.5 control with $NH_4OH$, and the temperature set to 30° C. At feed start, feed was added to maintain the DO setpoint at 40%. The DO setpoint was ramped down to 20% in a linear fashion over the following 24 hours by increased feed rate. The DO was then maintained at 20% via feed addition for the remainder of the fermentation.

TABLE 3 fermentation feeding protocol. Fermentation 2nd phase was always ~20% by weight Drakeol 5. For more explanation, see text.

| Run: | Batch: | Feed: |
|---|---|---|
| ethanol | 5% glucose (w/v)<br>1% ethanol (w/v) | 100% ethanol (w/v) |
| oil | 6.25% oleic acid (v/v)<br>1.4% corn oil (v/v) | 100% corn oil (w/v) |

Retinoid quantification. Analysis of retinoids were carried out with a C4 reverse phase retinoid method (see below) and C18 as described elsewhere (WO2020141168). The addition of all added intermediates gives the total amount of retinoids.

C4 reverse phase chromatography. For exact determination of discrete retinoids the long run reverse phase system was used. We separated analytes at 230 nm and 325 nm through the Agilent 1290 instrument with YMC Pro C4, 150×3.0 mm 3 µm column (YMC America, Devens, MA) stationary phase, and a 5 µl injection loop volume and column and sample tray controlled at 23° C. with gradients described in Table 4B. Analytes were detected at 230 nm and 325 nm and the peaks identity verified with LCMS. The analytes separated as discrete peaks that were assigned according to Table 4A.

TABLE 4A list of analytes using C4-reverse phase method. The addition of all added intermediates gives the total amount retinoids. "RT" means retention time. For more details, see text.

| Intermediates | RT [min] | λ max [nm] |
|---|---|---|
| trans-retinol | 20.21 | 325 |
| cis-retinol | 20.32 | 325 |
| dihydro-retinol | 20.75 | 290 |
| trans-retinal | 20.89 | 380 |
| cis-retinal | 21.02 | 380 |

TABLE 4A-continued list of analytes using C4-reverse phase method. The addition of all added intermediates gives the total amount retinoids. "RT" means retention time. For more details, see text.

| Intermediates | RT [min] | λ max [nm] |
|---|---|---|
| trans-retinyl-acetate | 22.15 | 325 |
| cis-retinyl-acetate | 22.35 | 325 |
| dihydro-retinyl acetate | 22.60 | 290 |
| retinyl esters | 26.30 | 325 |

TABLE 4B

UPLC Method Gradient with solvent A: acetonitrile; solvent B: water; solvent C: water/acetonitrile/methanesulfonic acid 1000:25:1. For more details, see text.

| Time [min] | % A | % B | % C | Flow [ml/min] |
|---|---|---|---|---|
| 0 | 5 | 85 | 10 | 0.5 |
| 20 | 98 | 0 | 2 | 0.5 |
| 35 | 98 | 0 | 2 | 0.5 |
| 35.1 | 5 | 85 | 10 | 0.5 |
| 40 | 5 | 85 | 10 | 0.5 |

Method Calibration. Method is calibrated using high purity retinyl acetate received from DSM Nutritional Products, Kaiseraugst, CH. Retinols and retinal are quantitated against retinyl acetate. Dilutions were prepared as follows. 40 mg of retinyl acetate was weighed into a 100 mL volumetric flask, and dissolved in ethanol, yielding a 400 µg/mL solution. This solution was sonicated as required to ensure dissolution. 5 mL of this 400 µg/mL solution was diluted into 50 mL (1/10 dilution, final concentration 40 µg/mL), 5 mL into 100 ml (1/20 dilution, final concentration 20 µg/mL), 5 ml of 40 µg/mL into 50 mL (1/10 dilution, final concentration 4 µg/mL), 5 mL of 20 µg/mL into 50 ml (1/10 dilution, 2 µg/mL), using 50/50 methanol/methyl tert-butyl ether (MTBE) as the dilutent. All dilutions were done in volumetric flasks. Purity of retinyl acetate was determined by further diluting the 400 µg/mL stock solution 100-fold (using a 2 mL volumetric pipet and a 200 mL volumetric flask) in ethanol. Absorbance of this solution at 325 nm using ethanol was taken as the blank, with adjustment of the initial concentration using the equation (Abs*dilution (100) *molecular weight (328.5)/51180=concentration in mg/ml). Because of quick out-maximization of UV absorbance of retinyl acetate, lower concentrations are better.

Sample preparation. Top second-phase layer samples from each strain were diluted at a 25-fold dilution or higher, if needed, into tetrahydrofuran (THF). Fermentation whole broth was prepared using a 2 mL Precellys (Bertin Corp, Rockville, MD) tube, adding 25 µl of well mixed broth and 975 µl of THF. Precellys (3×15×7500 rpm) for two cycles with a freeze at −80° C. for 10 minutes between cycles. Cell debris was spun down via centrifugation for 1 minute at 13000 rpm. These samples were diluted 10-fold in THF for analysis.

Example 2: Impact of Carbon Source on Retinoid Production in Fed-Batch Fermentations Using *Yarrowia*

To evaluate the impact of carbon source on the production of retinoids in *Yarrowia lipolytica*, fermentations in the presence of ethanol or oil (see Table 3) were run, and the purity as well as percentage of retinyl acetate assessed via measuring percentage of FARE from strain ML18812.

Fermentation in the presence of ethanol resulted in a strong reduction of FARE formation compared to fermentations in the presence of corn oil. Percentage of total retinoids as well as retinyl acetate could also be increased in comparison to corn oil fermentations. The results are shown in Table 5.

TABLE 5 effect of ethanol on production of FARE, retinoids and retinyl acetate ("retAc") using strain ML18812. "+++" is in the top quartile of the maximum value, "++" is in the mid quartile and "+/−" indicates trace amounts observed, while "−−−" indicates not observed, "retAc" means retinyl acetate. For more explanation, see text.

| Carbon source | Total retinoids | retAc | FAREs |
|---|---|---|---|
| Ethanol | +++ | +++ | −−− |
| corn oil | ++ | +/− | +++ |

The invention claimed is:

1. A process for production of retinyl acetate in a fungal host cell, wherein the host cell is a *Yarrowia* yeast cell, said process comprising fermentation of the host cell in the presence of ethanol.

2. The process according to claim 1 wherein the fermentation is a fed-batch fermentation.

3. The process according to claim 2 comprising a concentration of 5% or less (v/v) ethanol added to the cultivation medium during the batch phase.

4. The process according to claim 1, said process comprising fermentation of the host cell in the absence of triglycerides.

5. The process according to claim 1, wherein the formation of by-products including fatty acid retinyl esters (FAREs) is reduced by at least 50% based on total retinoids and compared to a process comprising fermentation of the host cell in the absence of ethanol.

6. The process according to claim 1, wherein the percentage of retinyl acetate based on total retinoids is increased by at least 25%, compared to a process comprising fermentation of the host cell in the absence of ethanol.

7. The process according to claim 1, wherein the production of total retinoids is increased by at least 30%, compared to a process comprising fermentation of the host cell in the absence of ethanol.

8. The process according to claim 1, wherein the host cell is transformed with and is expressing heterologous genes encoding acetylating enzymes catalyzing the conversion of retinol to retinyl acetate.

9. The process according to claim 8, wherein the acetylating enzyme comprises one or more amino acid substitution(s) located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof in a polypeptide according to SEQ ID NO:18.

10. A process for reduction of enzymatic conversion of retinol into FAREs with a percentage of FARE based on total retinoids being less than 25%, said process comprising fermentation of a retinyl acetate producing host cell in the presence of ethanol.

11. The process according to claim 1, said process comprising fermentation of the host cell in the absence of vegetable oil.

12. The process according to claim 1, wherein the host cell is transformed with and is expressing heterologous genes encoding fungal enzymes catalyzing the conversion of retinol to retinyl acetate.

13. The process according to claim 1, wherein the host cell is transformed with and is expressing heterologous genes originated from *Lachancea mirantina* encoding enzymes catalyzing the conversion of retinol to retinyl acetate.

* * * * *